US010383558B2

(12) United States Patent
Cho et al.

(10) Patent No.: US 10,383,558 B2
(45) Date of Patent: Aug. 20, 2019

(54) DEVICE FOR MEASURING BIO INFORMATION AND METHOD FOR MANUFACTURING THE SAME

(71) Applicant: Samsung Electronics Co., Ltd., Gyeonggi-do (KR)

(72) Inventors: Seong-Je Cho, Gyeonggi-do (KR); Kwang-Bok Kim, Incheon (KR); Jae-Geol Cho, Gyeonggi-do (KR); Chul-Ho Cho, Gyeonggi-do (KR); Hyoung-Seon Choi, Seoul (KR); Seok-Gin Kang, Gyeonggi-do (KR); Sun-Tae Jung, Gyeonggi-do (KR)

(73) Assignee: Samsung Electronics Co., Ltd. (KR)

( * ) Notice: Subject to any disclaimer, the term of this patent is extended or adjusted under 35 U.S.C. 154(b) by 551 days.

(21) Appl. No.: 15/063,003

(22) Filed: Mar. 7, 2016

(65) Prior Publication Data
US 2016/0256091 A1   Sep. 8, 2016

Related U.S. Application Data

(60) Provisional application No. 62/129,256, filed on Mar. 6, 2015.

(30) Foreign Application Priority Data

Oct. 5, 2015 (KR) .................. 10-2015-0140007

(51) Int. Cl.
*A61B 5/1486* (2006.01)
*A61B 5/00* (2006.01)
(Continued)

(52) U.S. Cl.
CPC ............ *A61B 5/14865* (2013.01); *A61B 5/01* (2013.01); *A61B 5/021* (2013.01); *A61B 5/024* (2013.01);
(Continued)

(58) Field of Classification Search
None
See application file for complete search history.

(56) References Cited

U.S. PATENT DOCUMENTS

2002/0187556 A1* 12/2002 Shartle ............... A61B 5/14514
436/149
2005/0215871 A1* 9/2005 Feldman ............ A61B 5/14514
600/309
(Continued)

FOREIGN PATENT DOCUMENTS

JP      2009-502261      1/2009
WO   WO 2000-035530   6/2000
(Continued)

OTHER PUBLICATIONS

International Search Report dated May 31, 2016 issued in counterpart application No. PCT/KR2016/002256, 7 pages.

*Primary Examiner* — Michael R Bloch
(74) *Attorney, Agent, or Firm* — The Farrell Law Firm, P.C.

(57) ABSTRACT

A bio information measuring device is provided. The bio information measuring device includes a sensor portion and a needle portion including a plurality of needles projecting from a plurality of openings formed in a surface of the sensor portion. The plurality of needles are configured to pierce tissue, wherein the plurality of needles include a biocompatible organic material which includes an enzyme member that reacts with an analysis material and a conductive polymer for transferring an electrical signal generated as a result of a reaction of the enzyme member with the analysis material.

17 Claims, 15 Drawing Sheets

(51) Int. Cl.
  *A61B 5/01* (2006.01)
  *A61B 5/021* (2006.01)
  *A61B 5/024* (2006.01)
  *A61B 5/0402* (2006.01)
  *A61B 5/145* (2006.01)

(52) U.S. Cl.
  CPC ......... *A61B 5/0402* (2013.01); *A61B 5/14546* (2013.01); *A61B 5/6824* (2013.01); *A61B 5/6848* (2013.01); *A61B 2562/125* (2013.01)

(56) References Cited

U.S. PATENT DOCUMENTS

| | | | |
|---|---|---|---|
| 2006/0211933 A1* | 9/2006 | Zimmermann | A61B 5/14514 600/352 |
| 2006/0264716 A1* | 11/2006 | Zander | A61B 5/14532 600/309 |
| 2007/0135698 A1* | 6/2007 | Shah | C12Q 1/006 600/348 |
| 2008/0033269 A1* | 2/2008 | Zhang | A61B 5/14532 600/347 |
| 2011/0144466 A1 | 6/2011 | Zhang | |
| 2011/0250510 A1 | 10/2011 | Cinquin et al. | |
| 2012/0016309 A1 | 1/2012 | Binks et al. | |
| 2013/0225956 A1* | 8/2013 | Huang | A61B 5/0537 600/345 |
| 2014/0259652 A1* | 9/2014 | Pushpala | G01N 27/3271 29/825 |
| 2014/0275897 A1 | 9/2014 | Pushpala et al. | |
| 2014/0336487 A1* | 11/2014 | Wang | A61B 5/685 600/352 |
| 2015/0208970 A1* | 7/2015 | Huang | A61B 5/685 600/345 |
| 2015/0208984 A1* | 7/2015 | Huang | A61B 5/685 600/393 |
| 2015/0208985 A1* | 7/2015 | Huang | A61B 5/150969 600/348 |
| 2016/0006039 A1 | 1/2016 | Cosnier et al. | |
| 2016/0157764 A1* | 6/2016 | Di Palma | A61B 5/14865 600/347 |

FOREIGN PATENT DOCUMENTS

| | | |
|---|---|---|
| WO | WO 2010/148441 | 12/2010 |
| WO | WO 2014/135787 | 9/2014 |

\* cited by examiner

DEVICE FOR MEASURING BIO INFORMATION AND METHOD FOR MANUFACTURING THE SAME

PRIORITY

This application claims priority under 35 U.S.C. § 119(e) to a U.S. Provisional Patent Application filed on Mar. 6, 2015 in the United States Patent and Trademark Office and assigned Ser. No. 62/129,256, and under 35 U.S.C. § 119(a) to a Korean Patent Application filed on Oct. 5, 2015 in the Korean Intellectual Property Office and assigned Serial No. 10-2015-0140007, the entire contents of both of which are incorporated herein by reference.

BACKGROUND

1. Field of the Disclosure

The present disclosure relates generally to a device for measuring bio information and a method for manufacturing the same, and more particularly, to a device for measuring bio information measuring that may remain stable even if micro needles are removed from a testee's corium and a method for manufacturing the same.

2. Description of the Related Art

Generally, needles are used to obtain specimens from a human body, detect a user's bio information, or administer medication. For these purposes, micro needles with a diameter of a few tens of millimeters are mostly used.

In particular, blood sugar readers such as blood sugar strips are used for diabetics to gather blood and read blood sugar levels (e.g., blood glucose levels) several times per day, like after waking-up and before and after meals. However, such blood sugar readers are required to use a lancet to gather blood from a testee upon each blood sugar level reading and to use a strip sensor and reader to measure the blood sugar level from the gathered blood.

In addition, a micro needle is provided to be left in a user's epidermis or corium for a predetermined time to enable a blood sugar level reading through body fluids in the epidermis or corium instead of requiring a testee to frequently gather blood to make a blood sugar level reading.

A device using micro needles to measure blood sugar (hereinafter, referred to as a "micro needle blood sugar reader") has a structure in which multiple micro needles placed on a base substrate are inserted into a testee's corium or epidermis to measure the testee's blood sugar level through the body fluids in the corium or epidermis.

Each micro needle includes a base needle projecting from the base substrate and formed of a material, e.g., silicone, and a catalyst and detecting layer along the outer circumferential surface of the base needle. If micro needles are inserted into a testee's corium or epidermis, while the micro needles are left in the corium or epidermis, or if the micro needles are removed from the corium or epidermis, the micro needles may detach from the base substrate and stick in the testee's corium or epidermis. In this case, the micro needles must either be left in the epidermis or removed, which causes the testee anxiety. Further, if micro needles are carried or processed, the catalyst and detecting layers coated on the outer circumferential surface of the base needles may partially detach from the base needles or lose the coating thereon. If the catalyst and detecting layers detach from the base needles, a resultant blood sugar level reading through the micro needles may have an increased error range or no blood sugar level may be measured. This may deteriorate the reliability of the micro needle blood sugar reader.

In terms of a process of manufacturing a micro needle blood sugar reader, base needles forming a shape of micro needles are formed on a base substrate, and conductive layers, detecting layers, and coating layers are disposed on an outer circumferential surface of the base needles. Thus, a process of manufacturing a micro needle blood sugar reader is complicated, and a stacking structure of a number of layers, including the conductive layers, detecting layers, and coating layers, may increase a defect rate of a micro needle blood sugar reader. Further, increasing the number of stacks on base needles increases the difficulty of reproducing base needles.

Moreover, it is difficult to efficiently arrange micro needles for working electrodes, reference electrodes, and counter electrodes.

Further, a micro needle blood sugar reader requires a packaging process for assembling working electrodes and other electrodes, e.g., reference electrodes and counter electrodes.

SUMMARY

An aspect of the present disclosure provides a bio information measuring device that may remain stable even if micro needles are removed from a testee's corium and a method for manufacturing the same.

Another aspect of the present disclosure provides a bio information measuring device that may correctly read blood sugar level through micro needles even if catalyst and detecting layers are removed from micro needles and a method for manufacturing the same.

Another aspect of the present disclosure provides a bio information measuring device that enables micro needles to be manufactured with a minimum number of processing steps and a method for manufacturing the same.

Another aspect of the present disclosure provides a bio information measuring device in which micro needles may be efficiently arranged on working electrodes or other electrodes and efficiently assembled and a method for manufacturing the same.

Another aspect of the present disclosure provides a needle portion that can be formed of a plurality of needles which are snapped out of a sensor portion and left in the epidermis or corium of the testee so that the plurality of needles may melt away in the epidermis or corium, thereby providing stability.

Another aspect of the present disclosure provides a method for obtaining bio information values in which, as the needle is formed as a single body of the mixture of the first member including the biocompatibility and conductive polymer and the second member including the enzyme member, even when an outer circumferential portion of the needle portion is removed or damaged while the needle portion is formed, processed, or carried, exact bio information values may be obtained without causing a difference in value regarding the needle portion between before and after measuring the bio information through the needle portion.

Another aspect of the present disclosure provides a needle in which the needle portion may be formed by injecting and forming a first member or second member while the sensor portion, e.g., the electrode portion and the substrate, the housing, and the mold portion are stacked, leading to a minimized number of the processes of manufacturing the bio information measuring device and securing the reproducibility upon manufacture of the micro needles.

Another aspect of the present disclosure provides a needle, in which the needle portion may be formed by injecting and forming the first member or second member while the sensor portion, e.g., the electrode portion and the substrate, the housing, and the mold portion are stacked, enabling the working electrode and other electrodes to be arranged in an efficient way and easier assembly thereof.

According to an aspect of the present disclosure, there is provided a bio information measuring device. The bio information measuring device includes a sensor portion and a needle portion including a plurality of needles projecting from a plurality of openings formed in a surface of the sensor portion. The plurality of needles are configured to pierce tissue, wherein the plurality of needles include a biocompatible organic material which includes an enzyme member that reacts with an analysis material and a conductive polymer for transferring an electrical signal generated as a result of a reaction of the enzyme member with the analysis material.

According to an aspect of the present disclosure, there is provided a method for manufacturing a bio information measuring device. The method includes stacking, on a substrate portion having a first space portion, a housing having a second space portion connected with the first space portion, stacking a mold portion having a concave needle tip shape on the housing, injecting, into at least one of a pair of openings provided under the substrate portion and connected with the first space portion, a biocompatible organic material including an enzyme member that reacts with an analysis material and a conductive polymer for transferring an electrical signal generated by a reaction of the enzyme member with the analysis material, polymerizing the biocompatible organic material including the enzyme member and the conductive polymer, which are injected up into the needle tip of the mold portion to form a needle portion, and removing the mold portion.

According to another aspect of the present disclosure, there is provided a needle member for measuring bio information. The needle member includes a plurality of needles configured to pierce tissue and formed as a single body, wherein the plurality of needles include a biocompatible organic material including an enzyme member that reacts with an analysis material and a conductive polymer for transferring an electrical signal generated by a reaction of the enzyme member with the analysis material.

Another aspect of the present disclosure provides a needle portion that can be formed of a plurality of needles which are snapped out of a sensor portion and left in the epidermis or corium of the testee so that the plurality of needles may melt away in the epidermis or corium, thereby providing stability.

Another aspect of the present disclosure provides a method for obtaining bio information values in which, as the needle is formed as a single body of the mixture of the first member including the biocompatibility and conductive polymer and the second member including the enzyme member, even when an outer circumferential portion of the needle portion is removed or damaged while the needle portion is formed, processed, or carried, exact bio information values may be obtained without causing a difference in value regarding the needle portion between before and after measuring the bio information through the needle portion.

Another aspect of the present disclosure provides a needle in which the needle portion may be formed by injecting and forming a first member or second member while the sensor portion, e.g., the electrode portion and the substrate, the housing, and the mold portion are stacked, leading to a minimized number of the processes of manufacturing the bio information measuring device and securing the reproducibility upon manufacture of the micro needles.

Another aspect of the present disclosure provides a needle, in which the needle portion may be formed by injecting and forming the first member or second member while the sensor portion, e.g., the electrode portion and the substrate, the housing, and the mold portion are stacked, enabling the working electrode and other electrodes to be arranged in an efficient way and easier assembly thereof.

BRIEF DESCRIPTION OF THE DRAWINGS

The above and other aspects, features, and advantages of the present disclosure will be more apparent from the following detailed description, taken in conjunction with the accompanying drawings, in which.

DETAILED DESCRIPTION

Figure 1:
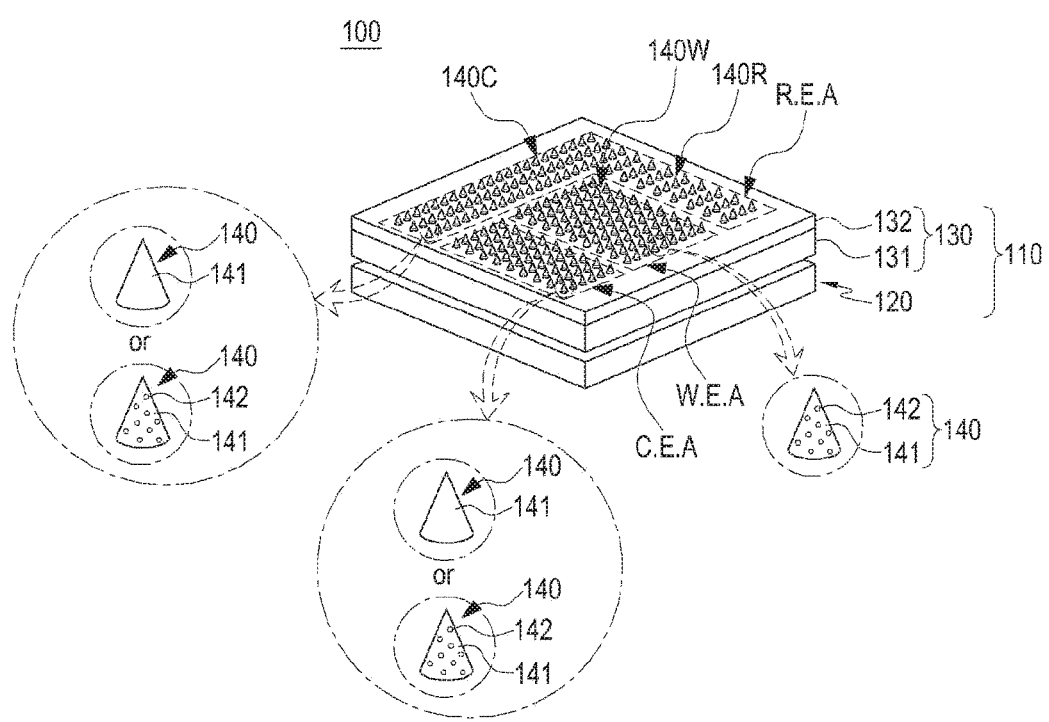
FIG. 1 is a perspective view of a bio information measuring device according to an embodiment of the present disclosure.

Various changes may be made to the present disclosure, and the present disclosure may describe a diversity of embodiments. Some embodiments of the present disclosure are shown and described in connection with the accompanying drawings. However, it should be appreciated that the present disclosure is not limited to the embodiments, and changes and/or equivalents or replacements thereto may also be within the scope and spirit of the present disclosure. The same or similar reference numerals may be used to refer to the same or similar elements throughout the specification and the accompanying drawings.

The terms concerning ordinal numbers such as "first" and "second" may be used to describe various components, but the components are not limited by the terms. The terms are used only to distinguish one component from another. For example, a first component may be referred to as a second component, and vice versa without departing from the scope and spirit of the present disclosure. The term "and/or" may refer to a combination(s) of a plurality of related items as listed or any of the items.

The terms "front surface," "rear surface," "upper surface," and "lower surface" are relative terms that may vary depending on directions in which figures are viewed, and may be replaced with ordinal numbers such as "first" and "second." The order denoted by ordinal numbers, e.g., first and second, may vary as necessary.

The terms used herein are provided merely to describe various embodiments of the present disclosure, but are not intended to limit the present disclosure. It is to be understood that the singular forms "a," "an," and "the" include plural references unless the context clearly dictates otherwise. It will be further understood that the terms "comprise" and/or "have," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms used herein have the same meanings as commonly understood by one of ordinary skill in the art to which the embodiments of the present disclosure belong. It will be further understood that terms, such as those defined in commonly used dictionaries, should be interpreted as having meanings that are consistent with their meanings in the context of the relevant art and should not be interpreted in an idealized or overly formal sense unless expressly so defined herein.

As used herein, the term "electronic device" may be any device with a touch panel, and an electronic device may also be referred to as a terminal, a portable terminal, a mobile terminal, a communication terminal, a portable communication terminal, a portable mobile terminal, or a display apparatus.

For example, an electronic device may be a smartphone, a mobile phone, a navigation device, a game device, a TV, a head unit for vehicles, a laptop computer, a tablet computer, a personal media player (PMP), or a personal digital assistant (PDA). An electronic device may be implemented as a pocket-sized portable communication terminal with a radio communication function. According to an embodiment of the present disclosure, an electronic device may be a flexible device or a flexible display.

An electronic device may communicate with an external electronic device, e.g., a server, or may perform tasks by communicating with an external electronic device. For example, an electronic device may transmit an image captured by a camera and/or location information detected by a sensor to a server through a network. A network may include, but is not limited to, a mobile or cellular communication network, a local area network (LAN), a wireless local area network (WLAN), a wide area network (WAN), the Internet, or a small area network (SAN).

FIG. 1 is a perspective view of a bio information measuring device 100 according to an embodiment of the present disclosure.

Figure 2:
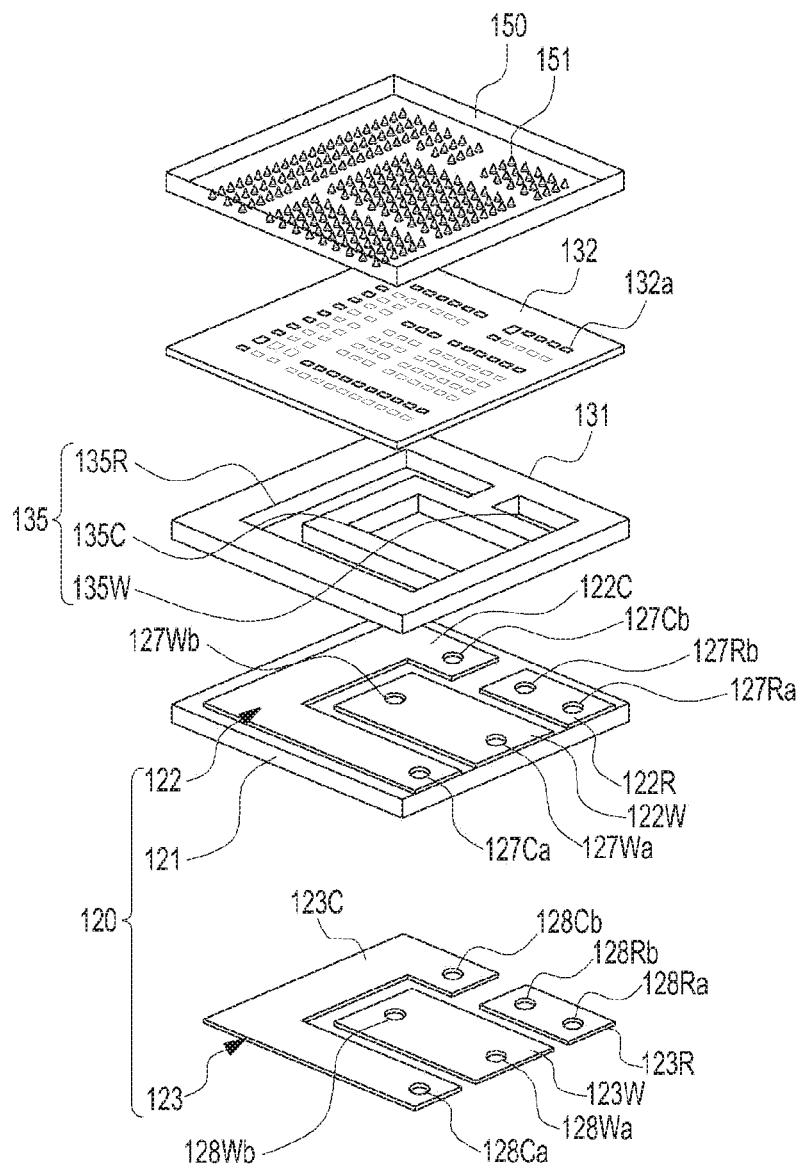
FIG. 2 is an exploded perspective view of a bio information measuring device according to an embodiment of the present disclosure.

FIG. 2 is an exploded perspective view of the bio information measuring device 100 according to an embodiment of the present disclosure.

Figure 3:
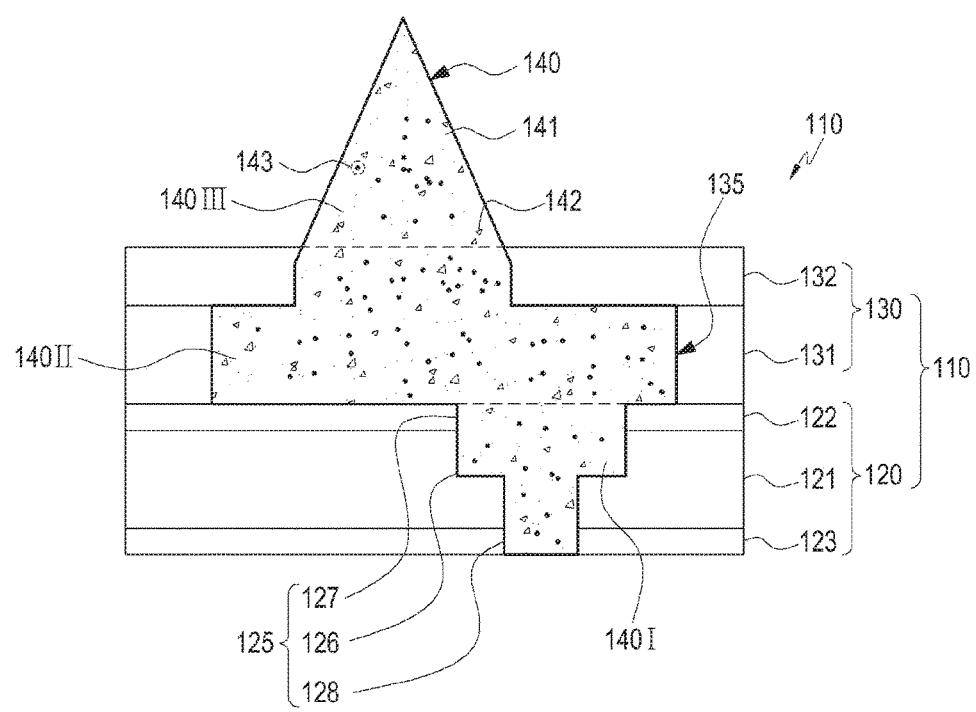
FIG. 3 is a cross-sectional view of a bio information measuring device according to an embodiment of the present disclosure.

FIG. 3 is a cross-sectional view of the bio information measuring device 100 according to an embodiment of the present disclosure.

Referring to FIGS. 1 to 3, the bio information measuring device 100 may include a sensor portion 110 and a needle portion 140. A mold portion 150 may be further included to form the needle portion 140 in a process of manufacturing the bio information measuring device 100.

The sensor portion 110 may receive bio information on a user (e.g. human H in FIG. 11 described below) detected through the needle portion 140 and detect various bio information. The sensor portion 110 may be formed so that the needle portion 140 projects from inside of the sensor portion 110 to a surface of the sensor portion 110. Inside the sensor portion 110 may be formed spaces where a base 140I and 140II of the needle portion 140 are provided, and the sensor portion 110 may be electrically connected through the base 140I and 140II of the needle portion 140. As described below, the needle portion 140 (also referred to as a needle member) may be formed of a biocompatible organic material 141 including a mixture of an enzyme member 142 and a conductive polymer 143. Further, the needle portion 140 may be formed to project from inside of the sensor portion 110 to a surface of the sensor portion 110 by polymerizing the biocompatible organic material 141 having the enzyme member 142 and the conductive polymer 143 mixture. The sensor portion 110 may be connected to a circuit portion, e.g., a communication module, via a connector to transfer bio information measured from the sensor portion 110 to a separate electronic device, e.g., a portable terminal, or to receive the same therefrom. An electronic device may store information received through the circuit portion or transmit stored information to the bio information measuring device 100. An electronic device may have a display module to display bio information, e.g., a testee's blood sugar level information, and may display various information, e.g., food intake according to a concentration of blood sugar of a user (H in FIG. 11 described below) therethrough. Further, an electronic device may be provided to create information detected by the bio information measuring device 100 as data in real-time, per date, or as numbers to be identified by a user (H in FIG. 11 described below).

The sensor portion 110 may include a substrate portion 120 and a housing 130. The substrate portion 120 may be disposed under the housing 130 and may have a first space portion 125 filled with a biocompatible organic material 141 including a mixture of the enzyme member 142 and the conductive polymer 143 which are described below or the biocompatible organic material 141 including the conductive polymer 143 without the enzyme member 142. The substrate portion 120 may include a main substrate 121 and an electrode portion 122 and 123, e.g., a first electrode 122 and a second electrode 123. The main substrate 121 may be disposed under the housing 130, and the electrode portion 122 and 123 may be disposed on at least one surface of the main substrate 121. For example, the electrode portion 122 and 123 may include the first electrode 122 and the second electrode 123 respectively disposed on the top and bottom of the main substrate 121 according to an embodiment of the present disclosure. However, the electrode portion 122 and 123 may be disposed only on the top or bottom of the main substrate 121. If the first electrode 122 and the second electrode 123 are disposed on the top and bottom, respectively, of the main substrate 121, the housing 130 may have the second electrode 123, the main substrate 121, and the first electrode 122 stacked from the bottom. Further, the base 140I and 140II of the needle portion 140 is connected to the first electrode 122 and the second electrode 123. The conductive polymer 143 in the needle portion 140 contacts and connects to the first electrode 122 and the second electrode 123 in the base 140I and 140II of the needle portion 140 to enable an electrical signal (or current) generated by a reaction of the enzyme member 142 to be transferred to the electrode portion 122 and 123.

Figure 4:
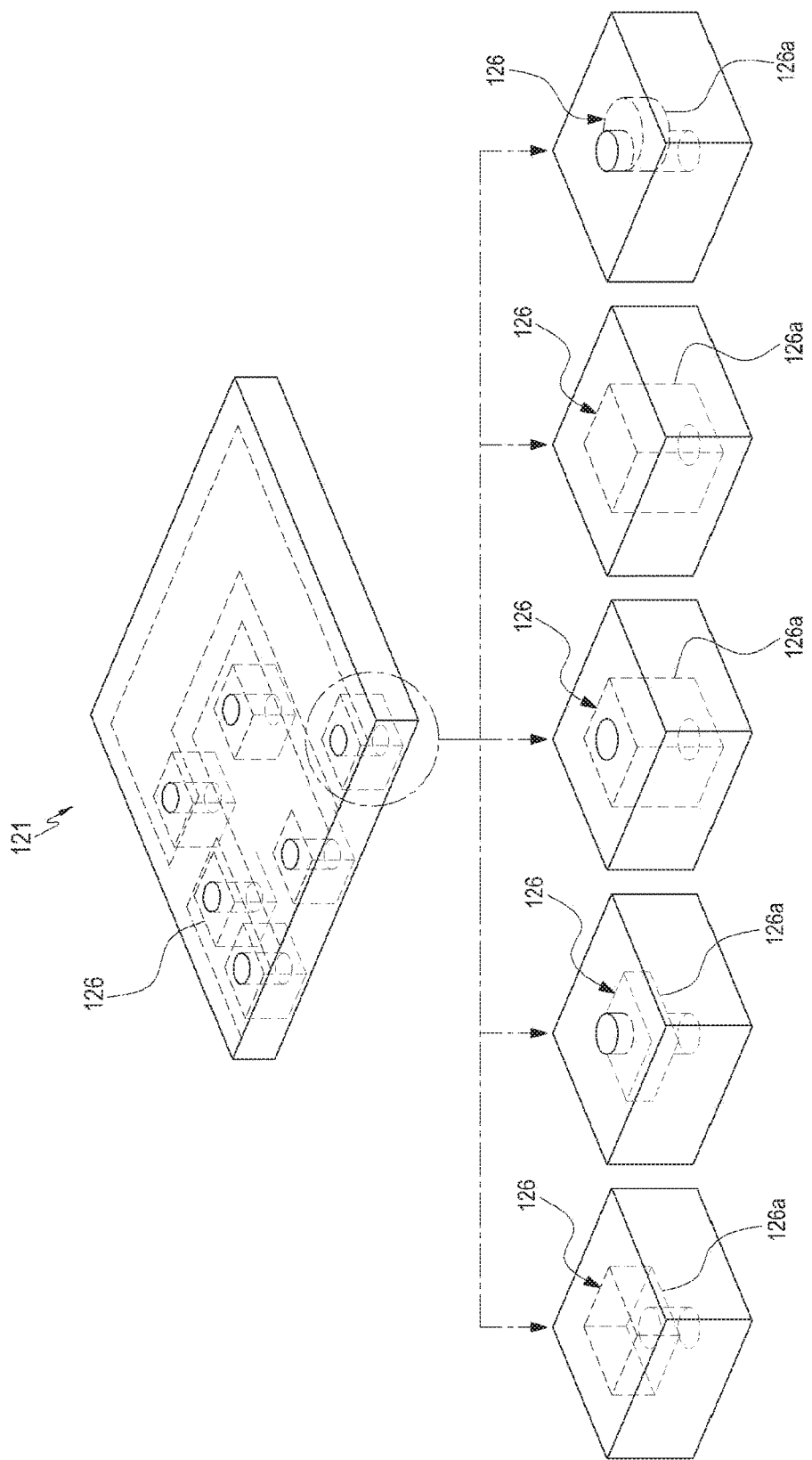
FIG. 4 is a diagram of a main substrate of a bio information measuring device according to an embodiment of the present disclosure.

FIG. 4 is a view of the main substrate 121 of the bio information measuring device 100 according to an embodiment of the present disclosure.

FIGS. 5A to 5D are views of various shapes of a reservoir 126a in the bio information measuring device 100 according to an embodiment of the present disclosure.

Figure 5A:
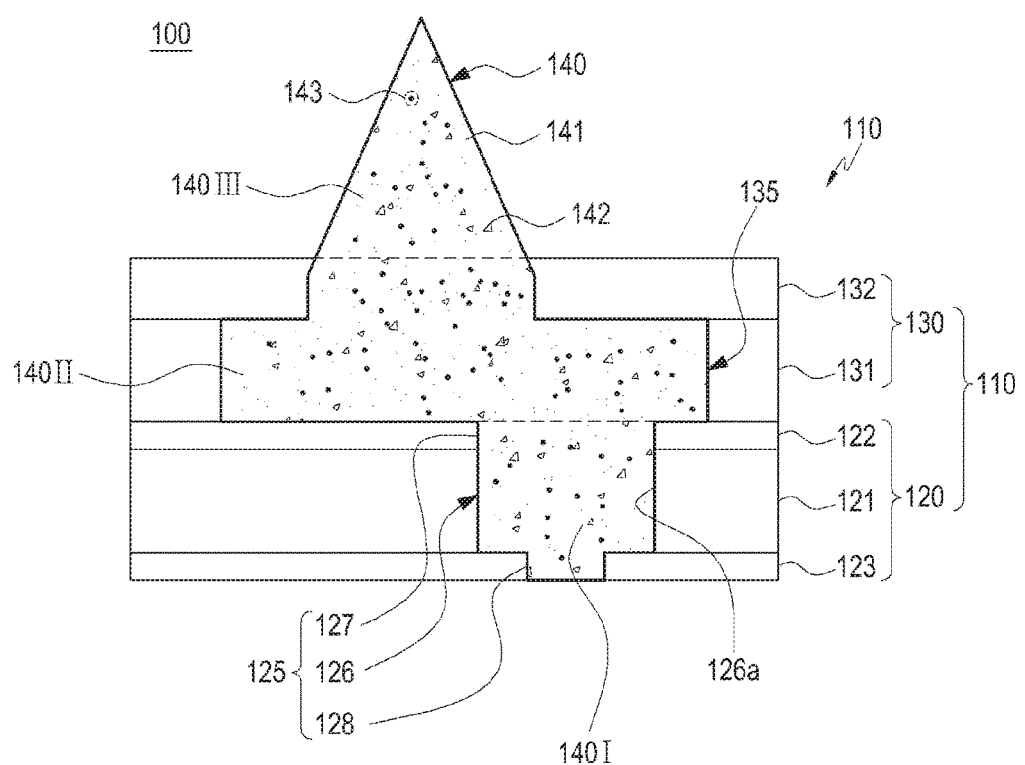
FIGS. 5A-5D are diagrams of various shapes of a reservoir in a bio information measuring device according to an embodiment of the present disclosure.
Figure 5B:
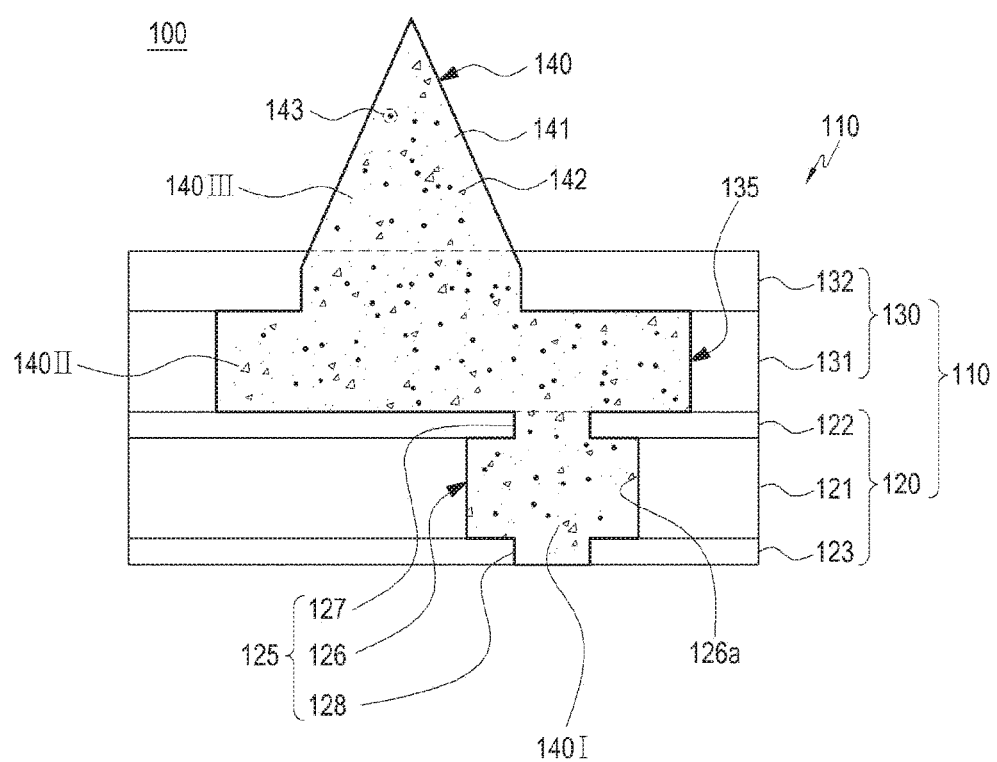
Figure 5C:
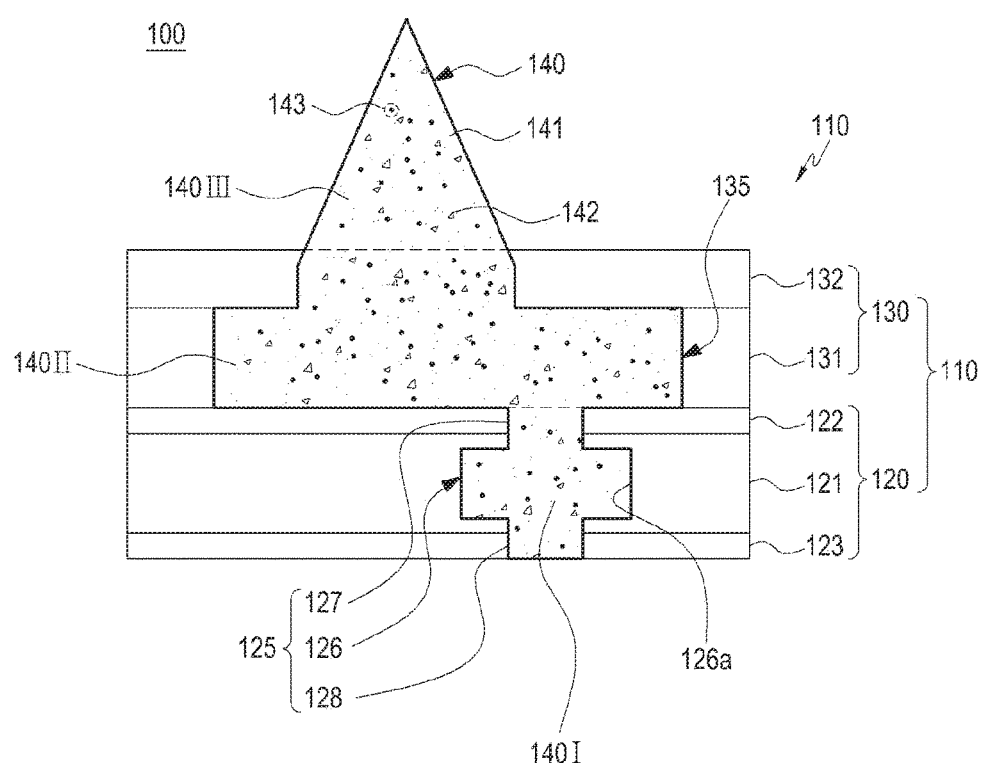
Figure 5D:
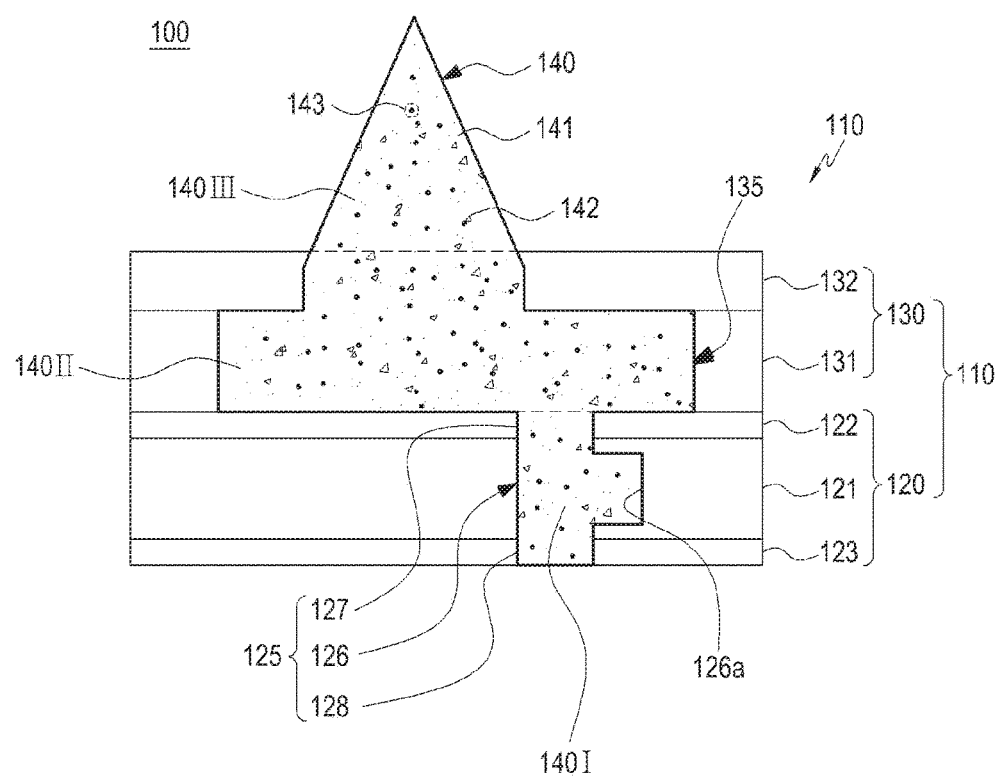

Referring to FIGS. 4 to 5D, the main substrate 121 may have a receiving portion 126 formed to be filled with the biocompatible organic material 141 including the enzyme member 142 and the conductive polymer 143 or the biocompatible organic material 141 including the conductive polymer 143. The above-described first and second electrodes 122 and 123 may be disposed on the top and bottom, respectively, of the main substrate 121. As described below, the receiving portion 126 may be provided to connect to a first opening 127 formed in the first electrode 122 and a second opening 128 formed in the second electrode 123. The receiving portion 126 may have a reservoir 126a. The reservoir 126a is a component for mitigating a change in volume that occurs when the biocompatible organic material 141 including the conductive polymer 143 and the enzyme member 142 introduced in the receiving portion 126 or the biocompatible organic material 141 including the conductive polymer 143 is formed.

Referring to FIG. 4, for example, the reservoir 126a according to an embodiment of the present disclosure is provided to be spaced apart from the second opening 128, which is described below, at a predetermined interval so that a broad space is formed on the first opening 127 side in the receiving portion 126 having the same size as the second opening 128. However, the shape of the reservoir 126a is not limited thereto.

Referring to FIG. 5A, for example, the reservoir 126a may be provided between the first opening 127 and the second opening 128 so that the receiving portion 126 is formed to be larger in size than the second opening 128 and the first opening 127 is formed to have a size corresponding to the receiving portion 126.

Referring to FIG. 5B, the reservoir 126a may be provided between the first opening 127 and the second opening 128 so that the receiving portion 126 is formed to be larger in size than the first opening 127 and the second opening 128.

Referring to FIG. 5C, the reservoir 126a may be provided so that the top and bottom of the receiving portion 126 are connected to the first opening 127 and the second opening 128, which are of the same size, where the reservoir 126a forms a broad space at a portion spaced apart from each of the first opening 127 and the second opening 128 between the first opening 127 and the second opening 128.

Referring to FIG. 5D, the reservoir 126a may be disposed between the first opening and the second opening to project in a direction from a side surface of the receiving portion 126 to form a space.

Figure 6A:
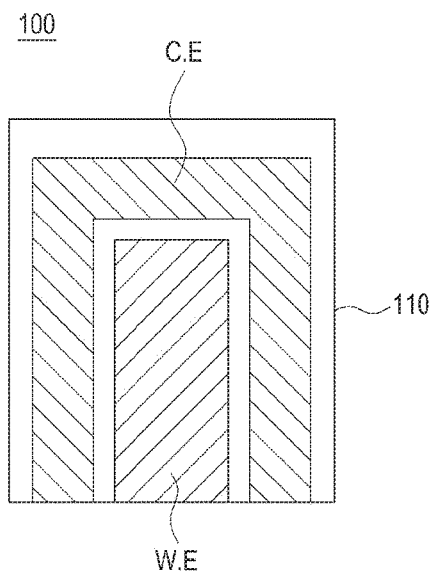
FIGS. 6A and 6B are diagrams of an electrode portion including two electrodes or three electrodes, respectively, in a bio information measuring device according to embodiments of the present disclosure.
Figure 6B:
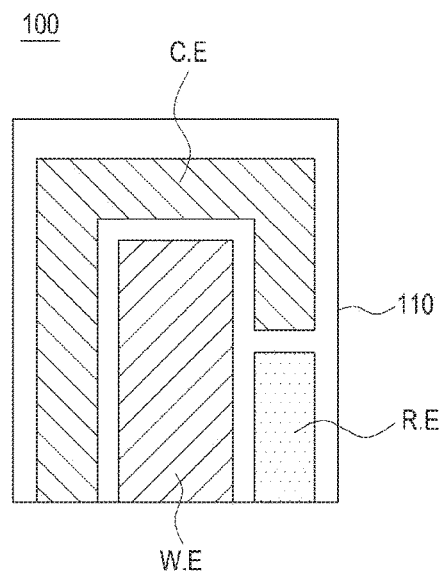

FIGS. 6A and 6B are views of an electrode portion 122 and 123 including two electrodes or three electrodes in the bio information measuring device 100 according to an embodiment of the present disclosure.

Referring to FIGS. 1-3, 6A, and 6B, the electrode portion 122 and 123 may be provided on the main substrate 121 and may include the first electrode 122 and the second electrode 123 on the top and bottom, respectively, of the main substrate 121. According to an embodiment of the present disclosure, the electrode portion 122 and 123 may have two electrodes or three electrodes to detect bio information signals. If the electrode portion 122 and 123 is provided with two electrodes, it may include working electrodes (W.E) 122W and 123W and counter electrodes (C.E) 122C and 123C surrounding the working electrodes (W.E) 122W and 123W. If the electrode portion 122 and 123 is provided with three electrodes, it may include working electrodes (W.E) 122W and 123W, counter electrodes (C.E) 122C and 123C surrounding the working electrodes (W.E) 122W and 123W, and reference electrodes (R.E) 122R and 123R surrounding the working electrodes (W.E) 122W and 123W and positioned opposite of ends of the counter electrodes (C.E) 122C and 123C. As described below, when the electrode portion 122 and 123 is provided with two electrodes, the needle portion 140 may be provided to connect corresponding to the respective positions of the two electrodes, but, according to the present disclosure, for example, the needle portion 140 is formed on the sensor portion 110 to be connected corresponding to the working electrodes (W.E) 122W and 123W of the two electrodes. When the electrode portion 122 and 123 is provided with three electrodes, the needle portion 140 may be provided to connect corresponding to the respective positions of the three electrodes, but, according to the present disclosure, for example, the needle portion 140 is formed on the sensor portion 110 to be connected corresponding to the working electrodes (W.E) 122W and 123W of the three electrodes.

Essentially, the working electrodes (W.E) are electrodes used to trigger a purported reaction and may are also be referred to as operation electrodes, task electrodes, or test electrodes. The working electrodes (W.E) may detect or measure various bio information, e.g., at least any one of glucose, lactic acid, body temperature, blood pressure, skin conductivity, heartbeat, electrocardiogram (ECG), cholesterol, minerals, disease biomarkers, cytokine, hormones, viruses, virus-derived materials, bacteria, or bacteria-derived materials, through the bio signals obtained through the needle portion 140.

The counter electrodes (C.E) are also called opposite electrodes and are electrodes installed to be positioned opposite the working electrodes (W.E) to enable electric current to flow through the working electrodes (W.E). The reference electrodes (R.E) are used to measure potentials. For example, upon measuring an electrode potential generated between a solution and a metal, its absolute value is impossible to measure. Thus, no change in the potential with the solution can be used as a reference and can be combined with the electrode to enable a relative value to be produced. The reference electrodes (R.E) are also referred to as comparison electrodes or electrodes for reference. When the electrode portion 122 and 123 is provided with two electrodes, the bio information signal may be computed by measuring the current generated from the potential between the working electrode (W.E) and the counter electrode (C.E). Conversely, when the electrode portion 122 and 123 is provided with three electrodes, the working electrodes (W.E) are provided (or configured) to measure electric signals, and the counter electrodes (C.E) are provided (or configured) to electrically connect to the working electrodes (W.E), and the reference electrodes (R.E) may be configured to supply a reference potential to the working electrodes (W.E) at ends of the counter electrodes (C.E).

When the electrode portion 122 and 123 is disposed on the top and bottom of the main substrate 121, the first electrode 122 may be provided on a surface (e.g., a first surface) of the main substrate 121 and may be electrically connected with the needle portion 140. Further, the second electrode 123 may be provided on a second surface (e.g., a surface of the main substrate that is disposed in opposing relation relative to the first surface) of the main substrate 121 and may be provided to connect with an external connector terminal of the bio information measuring device 100.

As described above, the first space portion 125 may be provided on the substrate portion 120 including the main substrate 121 and the first and second electrodes 122 and 123 (see FIGS. 3 and 4). The first space portion 125 may be provided with the receiving portion 126, the first opening 127, and the second opening 128.

The first opening 127, the receiving portion 126, and the second opening 128 may be coupled together with the first electrode 122, the main substrate 121, and the second electrode 123 stacked, forming a single first space portion 125. The biocompatible organic material 141 including the enzyme member 142 and the conductive polymer 143 or the biocompatible organic material 141 including the conductive polymer 143 fills the first space portion 125 upon formation, and the first electrode 122 and the second electrode 123 may be conducted by the biocompatible organic material 141 including the enzyme member 142 and the conductive polymer 143 or the biocompatible organic material 141 including the conductive polymer 143.

The receiving portion 126 is a component that passes through the inside of the main substrate 121 to form a space as described above. The receiving portion 126 may be provided with the same shape as the first opening 127 or the second opening 128 as described below. The receiving portion 126 is provided with the reservoir 126a to provide a predetermined space for a change in volume of the biocompatible organic material 141 including the enzyme member 142 and the conductive polymer 143 or the biocompatible organic material 141 including the conductive polymer 143.

The first opening 127 may be formed to pass through two opposite surfaces of the first electrode 122 and may be provided corresponding to the position of the receiving portion 126. The first opening 127 may be formed to connect the second space portion 135 to the receiving portion 126. The first opening 127 may be configured to inject the biocompatible organic material 141 including the enzyme member 142 and the conductive polymer 143 or the biocompatible organic material 141 including the conductive polymer 143, which is injected through the second opening 128 and the receiving portion 126 upon manufacturing the bio information measuring device 100, into the second space portion 135.

A pair of the first opening 127 may be provided at each electrode portion 122 and 123. For example, when the electrode portion 122 and 123 is formed with two electrodes, two first openings 127 may be formed at each of the working electrode (WE) and the counter electrode (C.E). When forming the needle portion 140 or first needle portion 140C or second needle portion 140R, one of the pair of first openings 127 may be provided as inlets 127Wa and 127Ca for injecting the biocompatible organic material 141 including the enzyme member 142 and the conductive polymer 143 or the biocompatible organic material 141 including the conductive polymer 143, and the other of the pair of the first openings 127 may be provided as air outlets 127Wb and 127Cb for discharging air filled in the first space portion 125 or the second space portion 135 upon filling the biocompatible organic material 141 including the enzyme member 142 and the conductive polymer 143 or the biocompatible organic material 141 including the conductive polymer 143. For example, when the electrode portion 122 and 123 is formed with three electrodes, two first openings 127 may be formed at each of the working electrode (W.E), the counter electrode (C.E), and the reference electrode (R.E). When forming the needle portion 140 or first needle portion 140C or second needle portion 140R, one of the pair of first openings 127 may be provided as inlets 127Wa, 127Ca, and 127Ra for injecting the biocompatible organic material 141 including the enzyme member 142 and the conductive polymer 143 or the biocompatible organic material 141 including the conductive polymer 143, and the other of the pair of the first openings 127 may be provided as air outlets 127Wb, 127Cb, and 127Rb for discharging air filled in the first space portion 125 or the second space portion 135 upon filling the biocompatible organic material 141 including the enzyme member 142 and the conductive polymer 143 or the biocompatible organic material 141 including the conductive polymer 143.

When the biocompatible organic material 141 including the enzyme member 142 and the conductive polymer 143 or the biocompatible organic material 141 including the conductive polymer 143 is formed while filling the first opening 127, the formed biocompatible organic material 141 including the enzyme member 142 and the conductive polymer 143 or the biocompatible organic material 141 including the conductive polymer 143 may electrically connect to the first electrode 122.

The second opening 128 may be formed on the second electrode 123. The second opening 128 may be configured to connect to the receiving portion 126 at a position corresponding to the receiving portion 126 and may be configured to inject the biocompatible organic material 141 including the enzyme member 142 and the conductive polymer 143 or the biocompatible organic material 141 including the conductive polymer 143 into the second space portion 135. A pair of the second openings 128 may be provided at each electrode portion 122 and 123. For example, when the electrode portion 122 and 123 is formed with two electrodes, two second openings 128 may be formed at each of the working electrode (W.E) and the counter electrode (C.E). When forming the needle portion 140 or first needle portion 140C or second needle portion 140R, one of the pair of second openings 128 may be provided as inlets 128Wa and 128Ca for injecting the biocompatible organic material 141 including the enzyme member 142 and the conductive polymer 143 or the biocompatible organic material 141 including the conductive polymer 143, and the other of the pair of the second openings 128 may be provided as air outlets 128Wb and 128Cb for discharging air filled in the first space portion 125 or the second space portion 135 upon filling the biocompatible organic material 141 including the enzyme member 142 and the conductive polymer 143 or the biocompatible organic material 141 including the conductive polymer 143. For example, when the electrode portion 122 and 123 is formed with three electrodes, two second openings 128 may be formed at each of the working electrode (W.E), the counter electrode (C.E), and the reference electrode (R.E). When forming the needle portion 140 or first needle portion 140C or second needle portion 140R, one of the pair of second openings 128 may be provided as inlets 128Wa, 128Ca, and 128Ra for injecting the biocompatible organic material 141 including the enzyme member 142 and the conductive polymer 143 or the biocompatible organic material 141 including the conductive polymer 143, and the other of the pair of the second openings 128 may be provided as air outlets 128Wb, 128Cb, and 128Rb for discharging air filled in the first space portion 125 or the second space portion 135 upon filling the biocompatible organic material 141 including the enzyme member 142 and the conductive polymer 143 or the biocompatible organic material 141 including the conductive polymer 143.

When the biocompatible organic material 141 including the enzyme member 142 and the conductive polymer 143 or the biocompatible organic material 141 including the conductive polymer 143 is formed in the second opening 128 while filling the first space portion 125 and the second space portion 135, the formed biocompatible organic material 141 including the enzyme member 142 and the conductive polymer 143 or the biocompatible organic material 141 including the conductive polymer 143 may electrically connect to the first electrode 122.

When bio information is introduced through the needle portion 140, e.g., when the enzyme member 142 provided in the needle portion 140 reacts with an analysis material in the body, the information of the reaction is delivered to the first electrode 122 and the second electrode 123. Here, it electrically connects to each of the base 140I and 140II of the needle portion 140 filling the first opening 127 and the base 140I and 140II of the needle portion 140 filling the second opening 128, so that the reaction information regarding the enzyme member 142 may be transferred to the electrode portion 122 and 123.

The housing 130 is a component stacked on the substrate portion 120, and in the housing 130, the second space portion 135 is connected to the first space portion. The needle portion 140 or the first needle portion 140C or second needle portion 140R may be formed to project to a surface of the housing 130 through the second space portion 135.

The housing 130 includes a first body 131 and a second body 132. The first body 131 may be referred to as a partitioning frame, and the second body 132 may be referred to as a fastening frame.

The first body 131 may be stacked on the substrate portion 120, e.g., the first electrode 122, and may form the second space portion 135 connected to the first space portion 125.

The second body 132 may be stacked on the first body 131, provided with a plurality of openings 132a (see FIG. 7) connected with the second space portion 135, and may be provided to fasten a plurality of needles 140 to the first body 131. Accordingly, the biocompatible organic material 141 including the enzyme member 142 and the conductive polymer 143 or the biocompatible organic material 141 including the conductive polymer 143 filling the second space portion 135 may be projected to a side of the sensor portion 110 through the openings 132a. The plurality of openings 132a provided in the second body 132 need not be provided at the same position or in the same number as the needle portions 140. Accordingly, various modifications or changes may be made to the second body 132 and the openings 132a provided in the second body 132 as long as the biocompatible organic material 141 including the enzyme member 142 and the conductive polymer 143 or the biocompatible organic material 141 including the conductive polymer 143 filling the second space portion 135 may be introduced into the needle tip 151, and as long as the biocompatible organic material 141 including the enzyme member 142 and the conductive polymer 143 or the biocompatible organic material 141 including the conductive polymer 143 filling the needle tip 151 can be formed through polymerization and is prevented from escaping or being removed from the second space portion 135. For example, the second body 132 can be provided as a mesh-shaped plate.

The second space portion 135 may be partitioned into two or three sections depending on the configuration of the electrode portion 122 and 123. That is, the second space portion 135 may be divided into a region corresponding to the position of the working electrode (W.E) and a region corresponding to other electrodes than the working electrode (W.E).

For example, as mentioned above, when the electrode portion 122 and 123 is provided with two electrodes, working electrode (W.E) and counter electrode (C.E), the second space portion 135 may be divided into two partitioned spaces, e.g., a first partitioned space 135W and a second partitioned space 135C. The first partitioned space 135W is a space provided corresponding to the position of the working electrode (W.E) and partitioned to fill a space on the position of the working electrode (W.E) with the biocompatible organic material 141 including the enzyme member 142 and the conductive polymer 143. The second partitioned space 135C is a space neighboring the first partitioned space 135W and filling a space on the counter electrode (C.E) with the biocompatible organic material 141 including the enzyme member 142 and the conductive polymer 143 or the biocompatible organic material 141 including the conductive polymer 143.

Further, as an example, when the electrode portion 122 and 123 is provided with three electrodes, e.g., working electrode (W.E), counter electrode (C.E), and reference electrode (R.E), the second space portion 135 may be divided into three partitioned spaces, e.g., a first partitioned space 135W, a second partitioned space 135C, and a third partitioned space 135R.

The first partitioned space 135W is a space provided corresponding to the position of the working electrode (W.E) and partitioned to fill a space on the position of the working electrode (W.E) with the biocompatible organic material 141 including the enzyme member 142 and the conductive polymer 143 or the biocompatible organic material 141 including the conductive polymer 143. The second partitioned space 135C is a space positioned around the first partitioned space 135W and is used for filling a space on the counter electrode (C.E) with the biocompatible organic material 141 including the enzyme member 142 and the conductive polymer 143 or the biocompatible organic material 141 including the conductive polymer 143. The third partitioned space 135R is a space disposed neighboring the first partitioned space 135W and the second partitioned space 135C, e.g., positioned at a side of an end of the second partitioned space 135C, and partitioned to fill a space on the reference electrode (R.E) with the biocompatible organic material 141 including the enzyme member 142 and the conductive polymer 143 or the biocompatible organic material 141 including the conductive polymer 143.

The first body 131 is a component that is configured to divide the electrode portion 122 and 123, depending on functionalities upon forming the needle portion 140 or the first needle portion 140C or second needle portion 140R.

Further, the second body 132 is provided with a plurality of openings 132a (FIG. 7) at the position corresponding to each electrode portion 122 and 123. The plurality of openings 132a are configured to enable the needle portion 140 to project therethrough while the biocompatible organic material 141 including the enzyme member 142 and the conductive polymer 143 or the biocompatible organic material 141 including the conductive polymer 143 is introduced through the second space portion 135, thereby allowing the formed needle portion 140 to project upwards through the plurality of opening 132a and to fasten to or support the base 140I and 140II of the needle portion 140 disposed inside the sensor portion 110, e.g., the base 140I and 140II of the needle portion 140 provided in the partitioned space of the second space portion 135 to prevent them from escaping from the substrate portion 120 and the housing 130.

According to an embodiment of the present disclosure, the needle portion 140 may be provided to first fill the first space portion 125 and second space portion 135 in the sensor portion 110 (hereinafter, referred to as needle portion base 140I and 140II) and to project to a surface of the sensor portion 110, e.g., the housing 130 (hereinafter, referred to as a micro needle portion 140III).

The needle portion 140, e.g., the micro needle portion 140III, may be provided to project from the sensor portion 110 to insert into or pierce the corium H2 of the user (H, see FIGS. 3 and 11, for example), and the needle portion base 140I and 140II and the micro needle portion 140III may be formed for filling the first and second space portions 125 and 135 as one body. The needle portion 140, particularly the micro needle portion 140III, may be formed of a material including the biocompatible organic material 141a that may melt out of the skin (or dissolve therein) even when inserted and left in the skin of the user (FIG. 11), e.g., the corium H2, and removed or escaped from the sensor portion 110.

The needle portion 140 may be formed of the biocompatible organic material 141 including the enzyme member 142 and the conductive polymer 143 or the biocompatible organic material 141 including the enzyme member 142 and the conductive polymer 143 using one or more polymerization methods.

Figure 7:
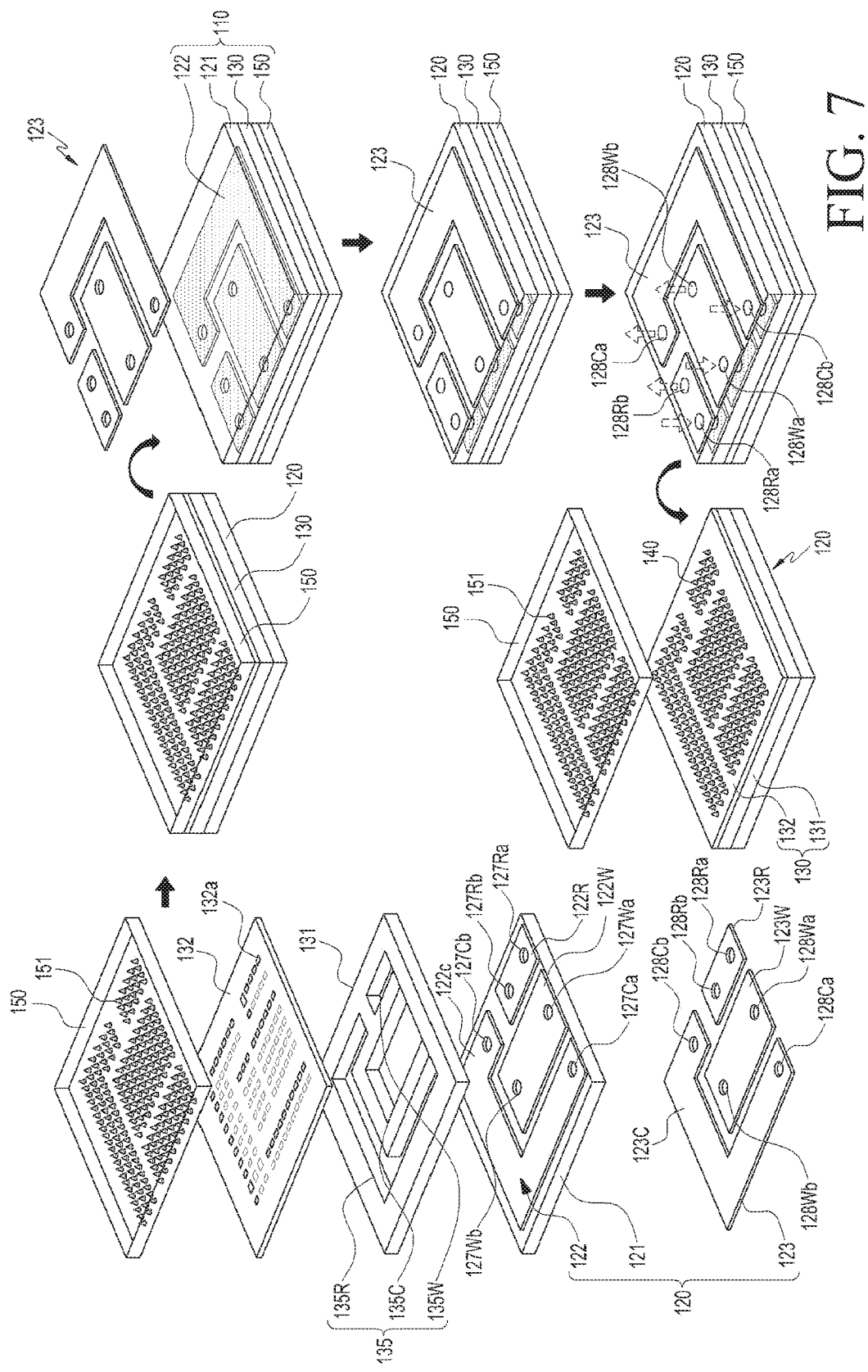
FIG. 7 is a perspective view of a process for manufacturing a bio information measuring device according to an embodiment of the present disclosure.
Figure 8:
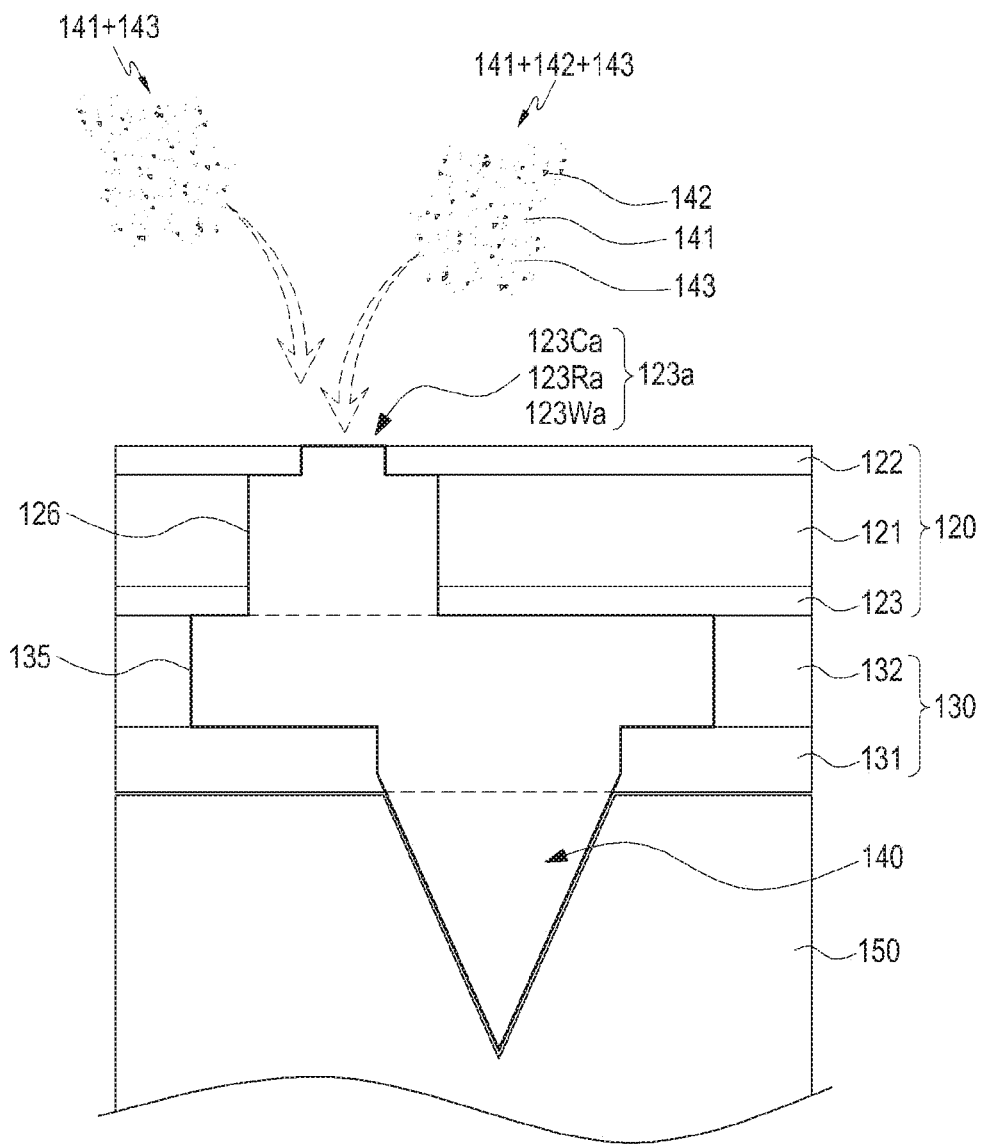
FIG. 8 is a diagram of a needle portion in a bio information measuring device according to an embodiment of the present disclosure.

The biocompatible organic material 141 including the enzyme member 142 and the conductive polymer 143, in a liquid phase, can be injected into a mold portion 150 stacked on the sensor portion 110 through the opening formed in the rear surface of the sensor portion 110, so as to form the needle portion 140 or the first needle portion 140C or second needle portion 140R projecting from inside of the sensor portion 110 to a surface thereof (see FIGS. 7 and 8, for example). A process of manufacturing the needle portion 140 or the first needle portion 140C or second needle portion 140R is described in greater detail below.

As described above, according to an embodiment of the present disclosure, the needle portion 140 is disposed in the working electrode area (W.E.A) connected with the working electrode (WE), and thus, it is formed of the biocompatible organic material 141 including the enzyme member 142 and the conductive polymer 143. Specifically, since the working electrode (W.E) is a component that detects information generated as the enzyme member 142 reacts with the body fluids, the needle portion 140 is disposed on the working electrode (W.E), connects to the working electrode (W.E), and contains the enzyme member 142.

Accordingly, the needle portion 140 corresponding to the position of the working electrode (W.E) should be formed of the biocompatible organic material 141, having biocompatibility 141a, and including the enzyme member 142 and the conductive polymer 143. However, the first needle portion 140C or second needle portion 140R provided at the position other than that of the working electrode (W.E), e.g., the counter electrode (C.E) or reference electrode (R.E), may be formed of the biocompatible organic material 141 where the enzyme member 142 and the conductive polymer 143 are mixed, or may be formed of the biocompatible organic material 141 including the conductive polymer 143 but excluding the enzyme member 142.

While the needle portion 140, which is provided at the position of the working electrode (W.E), has been described as being formed as a one body including the biocompatible organic material 141 having the enzyme member 142 and the conductive polymer 143 mixed, the present disclosure is not so limited. For example, the enzyme member 142 or the biocompatible organic material 141 having the enzyme member 142 and the conductive polymer 143 mixed may be coated on the outer surface of the body formed with the biocompatible organic material 141 including the conductive polymer 143. As can be appreciated, various changes or modifications to the needle portion 140 disposed on the working electrode (W.E) may be made as long as the needle portion 140 is configured to have the enzyme member 142 be able to react with the reactive substances in the body.

In contrast, the first needle portion 140C or second needle portion 140R disposed on the counter electrode (C.E) or reference electrode (R.E) need not react with the reactive substances in the body, and, therefore, the first needle portion 140C or second needle portion 140R may be formed of a stable material that melts away or dissolves in the body when the micro needle portion 140III is snapped and left in the body. Thus, the first needle portion 140C or second needle portion 140R disposed on the counter electrode (C.E) or reference electrode (R.E) may be formed of the biocompatible organic material 141a including the conductive polymer 143 but not including the enzyme member 142. As can be appreciated, the first needle portion 140C or second needle portion 140R can be formed similarly to the needle portion 140.

The needle portion 140 may be disposed at the position on the working electrode (W.E) and electrodes other than the working electrode (W.E) depending on the functionalities of the electrode portion 122 and 123. Conversely, the first needle portion 140C and/or the second needle portion 140R may be separately partitioned from the needle portion 140 and disposed at a position of an electrode other than the working electrode (W.E).

For example, when the electrode portion 122 and 123 is provided with two electrodes, the needle portion 140 may be disposed at a position on the working electrode (W.E) and the counter electrode (C.E), and unlike this, the needle portion 140 may be disposed at the position of the working electrode (W.E) while the first needle portion 140C disposed at a position on the counter electrode (C.E).

When the electrode portion 122 and 123 is provided with two electrodes, the top surface of the housing 130 may be partitioned into a working electrode area (W.E.A) that connects to the working electrode (W.E) and a counter electrode area (C.E.A) that neighbors the working electrode area (W.E.A) and is positioned corresponding to the position of the counter electrode (C.E).

A working needle portion 140W may be provided to project (or extend) from the working electrode area (W.E.A). Further, the working needle portion 140W may connect to the first partitioned space 135W on the working electrode area (W.E.A). The working needle portion 140W may project to a side of the sensor portion 110 from inside of the sensor portion 110 as the biocompatible organic material 141 including the enzyme member 142 and the conductive polymer 143 is formed. The overall working needle portion 140W, i.e., the needle portion base 140I and 140II and the micro needle portion 140III, may be provided as one body. Although the working needle portion 140W has been described as a single body formed of the biocompatible organic material 141 including the conductive polymer 143, the working needle portion 140W may be provided with a coating including the enzyme member 142 including the conductive polymer 143 along the outer surface of the working needle portion 140W projecting to a side of the sensor portion 110 (corresponding to the micro needle portion 140III).

The first needle portion 140C may project from the counter electrode area (C.E.A). Further, the first needle portion 140C may connect to the second partitioned space 135C on the counter electrode area (C.E.A). The first needle portion 140C may project from inside of the sensor portion 110 to a side of the sensor portion 110 by forming the biocompatible organic material 141 including the enzyme member 142 and the conductive polymer 143 or the biocompatible organic material 141 including the conductive polymer 143. The first needle portion 140C may be provided as a single body, as described above with respect to needle portion 140.

Further, when the electrode portion 122 and 123 is provided with three electrodes, the needle portion 140 may be disposed on the working electrode (W.E), counter electrode (C.E), and reference electrode (R.E). Alternatively, the needle portion 140 may be disposed on the working electrode (W.E), the first needle portion 140C on the counter electrode (C.E), and the second needle portion 140R on the reference electrode (R.E).

When the electrode portion 122 and 123 is provided with three electrodes, the top surface of the housing 130 may be partitioned into a working electrode area (W.E.A) connecting to the working electrode (W.E), a counter electrode area (C.E.A) that is positioned around the working electrode area (W.E.A) and provided at a position corresponding to the position of the counter electrode (C.E), and a reference electrode area (R.E.A) that neighbors the working electrode area (W.E.A) at an end of the counter electrode area (C.E.A) and is positioned corresponding to the position of the reference electrode (R.E).

The working needle portion 140W may project from the working electrode area (W.E.A). Further, the working needle portion 140W may connect to the first partitioned space 135W on the working electrode area (W.E.A). The working needle portion 140W project to a side of the sensor portion 110 from inside of the sensor portion 110 as the biocompatible organic material 141 including the enzyme member 142 and the conductive polymer 143 is formed. The working needle portion 140W may be provided as one body, which has been previously described. However, the working needle portion 140W may be provided so that the biocompatible organic material 141 including the conductive polymer 143 is formed to project from inside of the sensor portion 110 to a side of the sensor portion 110 and the enzyme member 142 or the biocompatible organic material 141 including the enzyme member 142 and the conductive polymer 143 is coated along the outer surface thereof.

The first needle portion 140C may project from the counter electrode area (C.E.A). Further, the first needle portion 140C may connect to the second partitioned space 135C on the counter electrode area (C.E.A). The first needle portion 140C may project to a side of the sensor portion 110 from inside of the sensor portion 110 as the biocompatible organic material 141 including the enzyme member 142 and the conductive polymer 143 is formed. The first needle portion 140C may be provided as one body. Although the first needle portion 140C has been described as being formed only of the biocompatible organic material 141 having the enzyme member 142 and the conductive polymer 143 mixed, the first needle portion 140C may be formed of the biocompatible organic material 141 including the conductive polymer 143 but not including the enzyme member 142.

The second needle portion 140R may project from the reference electrode area (R.E.A). Further, the second needle portion 140R may connect with the third partitioned space 135R on the reference electrode area (R.E.A). The second needle portion 140R may project to a side of the sensor portion 110 from inside of the sensor portion 110 as the biocompatible organic material 141 including the enzyme member 142 and the conductive polymer 143 is formed. The second needle portion 140R may be provided as one body. Although the second needle portion 140R has been described as being formed of the biocompatible organic material 141 having the enzyme member 142 and the conductive polymer 143 mixed, the second needle portion 140R, like the first needle portion 140C, may be formed of the biocompatible organic material 141 including the conductive polymer 143 but not including the enzyme member 142.

FIG. 7 is a perspective view illustrating a process for manufacturing a bio information measuring device 100, according to an embodiment of the present disclosure. FIG. 8 illustrates an example of forming a needle portion 140 in a bio information measuring device 100, according to an embodiment of the present disclosure.

Referring to FIGS. 7 and 8, the needle portion 140, as described above, is a single-bodied component of needles projecting from inside of the sensor portion 110, e.g., the first space portion 125 and the second space portion 135, to a side of the sensor portion 110. The needle portion 140 may project from or extend through the plurality of openings 132a formed on a surface of the sensor portion 110.

In order to form the needle portion 140 (hereinafter, the working needle portion 140W, the first needle portion 140C, and the second needle portion 140R are collectively referred to as the needle portion 140) as a single body on the sensor portion 110, the mold portion 150 is stacked on the sensor portion 110 having the substrate portion 120 and the housing 130 stacked, and the biocompatible organic material 141 including the enzyme member 142 and the conductive polymer 143 or the biocompatible organic material 141 including the conductive polymer 143 is injected through the opening formed in the rear surface of the sensor portion 110 and is then polymerized to form the single-bodied needle portion 140.

In order to form the needle portion 140 on the sensor portion 110, the mold portion 150 may be stacked on the housing 130, with the substrate portion 120 and the housing 130 stacked one over another. A plurality of concave needle tips 151 corresponding to the position of the electrode portion 122 and 123 may be formed on an inner surface of the mold portion 150, e.g., a surface where the mold portion 150 faces the housing 130, to form the shape of the needle portion 140. The needle tips 151 formed on the mold portion 150 are partitioned for their arranged areas depending on the way the electrode portion 122 and 123 is disposed, e.g., depending on the arrangement of two electrodes or three electrodes. The mold portion 150 is a component that forms the needle portion 140 by projecting, to a side surface of the sensor portion 110, the biocompatible organic material 141 including the enzyme member 142 and the conductive polymer 143 or the biocompatible organic material 141 including the conductive polymer 143 injected through the first space portion 125 and the second space portion 135. The mold portion 150 is then removed from the sensor portion 110 after polymerization takes place. The needle tips 151 may be sized so that the base of the needle portion 140 measures 30 um to 300 um on the surface of the sensor portion 110, and an apex of the needle portion 140 measures 200 um to 1,000 um from the base.

As the mold portion 150 is stacked on the sensor portion 110, the second electrode 123, the main substrate 121, the first electrode 122, the first body 131, the second body 132, and the mold portion 150 are stacked in this order. Further, as the sensor portion 110 and the mold portion 150 are stacked in such manner, the second opening 128 of the second electrode 123, the first opening 127, the second space portion 135, and the needle tips 151 may be connected together such that the needle tips 151 can pass through the second opening 128 and the first opening 127.

Here, when the biocompatible organic material 141 including the enzyme member 142 and the conductive polymer 143 or the biocompatible organic material 141 including the conductive polymer 143 is injected through the second opening 128, the biocompatible organic material 141 including the enzyme member 142 and the conductive polymer 143 or the biocompatible organic material 141 including the conductive polymer 143 is injected into the receiving portion 126, the first opening 127, and the second space portion 135 and fills the first space portion 125 and the second space portion 135 inside the sensor portion 110. Further, the biocompatible organic material 141 including the enzyme member 142 and the conductive polymer 143 or the biocompatible organic material 141 including the conductive polymer 143 fully filling the first space portion 125 and the second space portion 135 may flow into the needle tips 151 through the opening of the housing 130 to form the needle portion 140.

After filling the first space portion 125, the second space portion 135, and the needle tips with the biocompatible organic material 141 including the enzyme member 142 and the conductive polymer 143 or the biocompatible organic material 141 including the conductive polymer 143, the biocompatible organic material 141 including the enzyme member 142 and the conductive polymer 143 or the biocompatible organic material 141 including the conductive polymer 143 may be polymerized into formed bodies of the sensor portion 110 and the needle portion 140 projecting from a side of the sensor portion 110.

The biocompatible organic material 141 including the enzyme member 142 and the conductive polymer 143 or the biocompatible organic material 141 including the conductive polymer 143, which is in a flowable state, may be formed by using at least one of electrical polymerization, thermal polymerization, photo polymerization, acid polymerization, or base polymerization. In particular, when the enzyme member 142 is mixed in the biocompatible organic material 141, the formed body may be made by electrical polymerization among the above polymerization methods to prevent damage to the enzyme member 142 in the polymerization process.

When the polymerization is complete, the needle portion 140 may be provided projecting to a side of the sensor portion 110 while filling the inside of the sensor portion 110, i.e., the first space portion 125 and the second space portion 135.

The conductive polymer 143 may include at least one material of polypyrrole, poly aniline, polyacetylene, polyphenylene, polyphenylene vinylene, polythiophene, polydiacetylene, and poly(3,4-ethylenedioxythiophene) (PEDOT).

As described above, the conductive polymer 143 included in the needle portion 140 may be utilized as sensor electrode on the surface of the micro needle portion 140III, and the conductive polymer 143 may be provided to make electrical connections between pieces of the electrode portion 122 and 123 on the surface of the micro needle portion 140III. Further, as the enzyme member 142, a material having selectivity to a material to be measured among the bio information may be used.

Further, the biocompatible organic material 141 including the enzyme member 142 and the conductive polymer 143 or the biocompatible organic material 141 including the conductive polymer 143 may further include a filler. The material of the filler may be comprised of all the biocompatible material occupying volume, and the material of the filler may include at least of poly(lactic acid)(PLA), poly(D, L-lactic acid)(PDLLA), poly(lactic-co-glycolic)(PLGA), poly(ethylene glycol)(PEG), poly(dimethylsiloxane) (PDMS), polycaprolactone etc.

When the biocompatible organic material 141 including the enzyme member 142 and the conductive polymer 143 or the biocompatible organic material 141 including the conductive polymer 143 is polymerized while filling the first space portion 125, the second space portion 135, and the needle tips 151, a change in volume of these components may occur. The filler may be added to the biocompatible organic material 141 including the enzyme member 142 and the conductive polymer 143 or the biocompatible organic material 141 including the conductive polymer 143 to adjust the change in volume occurring in the process of polymerizing the biocompatible organic material 141 including the enzyme member 142 and the conductive polymer 143 or the biocompatible organic material 141 including the conductive polymer 143.

Further, the above-mentioned receiving portion 126, e.g., the reservoir 126a formed in the receiving portion 126, may adjust the change in volume in the process of polymerizing the biocompatible organic material 141 including the enzyme member 142 and the conductive polymer 143 or the biocompatible organic material 141 including the conductive polymer 143 filling the first space portion 125. That is, the receiving portion 126 may be configured to expand and contract during the polymerization process.

Figure 9:
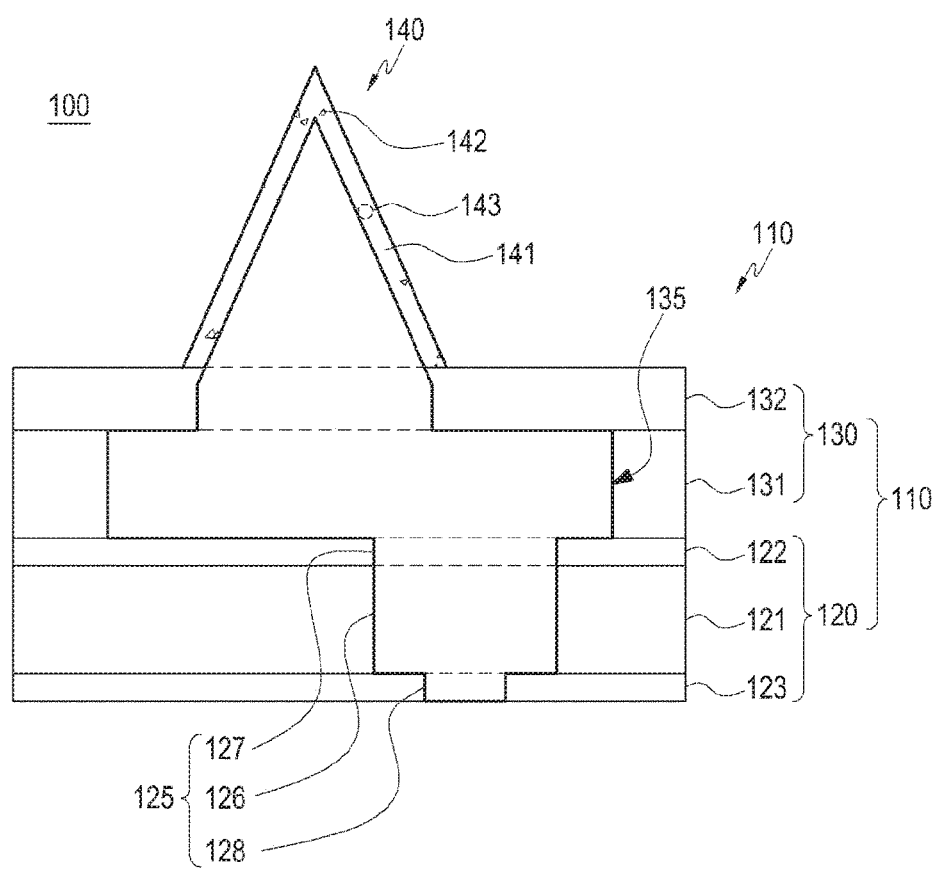
FIG. 9 is a diagram a shape of a needle portion in a bio information measuring device according to an embodiment of the present disclosure.

FIG. 9 is a diagram of the needle portion 140 in the bio information measuring device 100 according to an embodiment of the present disclosure.

Referring to FIG. 9, the needle portion 140 may be formed of the biocompatible organic material 141 including the conductive polymer 143 but excluding the enzyme member 142, and in this instance, the first needle portion 140C or the second needle portion 140R may be formed only of the above material, but the working needle portion 140W can include the enzyme member 142 that may react with the reactive substance in the body. Thus, the working needle portion 140W may be provided so that the enzyme member 142 or the biocompatible organic material 141 including the enzyme member 142 and the conductive polymer 143 is coated on the outer surface of the micro needle portion 140III formed of the biocompatible organic material 141 including the conductive polymer 143 which projects to a side of the sensor portion 110. The portion having the micro needle portion 140III coated with the enzyme member 142 may be the portion disposed on the working electrode area (W.E.A).

Accordingly, upon stacking the needle portion 140 on the sensor portion 110, the biocompatible organic material 141 including the conductive polymer 143 may be injected to form needles, and then, the enzyme member 142 or the biocompatible organic material 141 including the enzyme member 142 and the conductive polymer 143 may be implemented only on the needles on the working electrode area (W.E.A).

Figure 10:
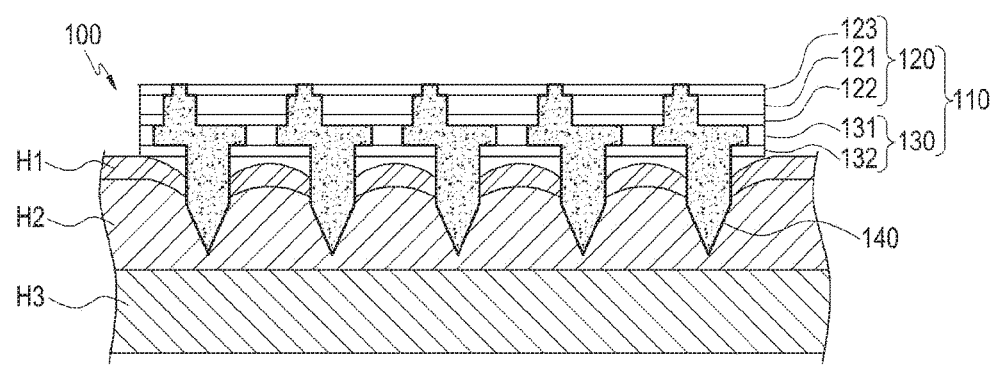
FIG. 10 is a diagram of a bio information measuring device inserted in a user's corium according to an embodiment of the present disclosure.
Figure 11:
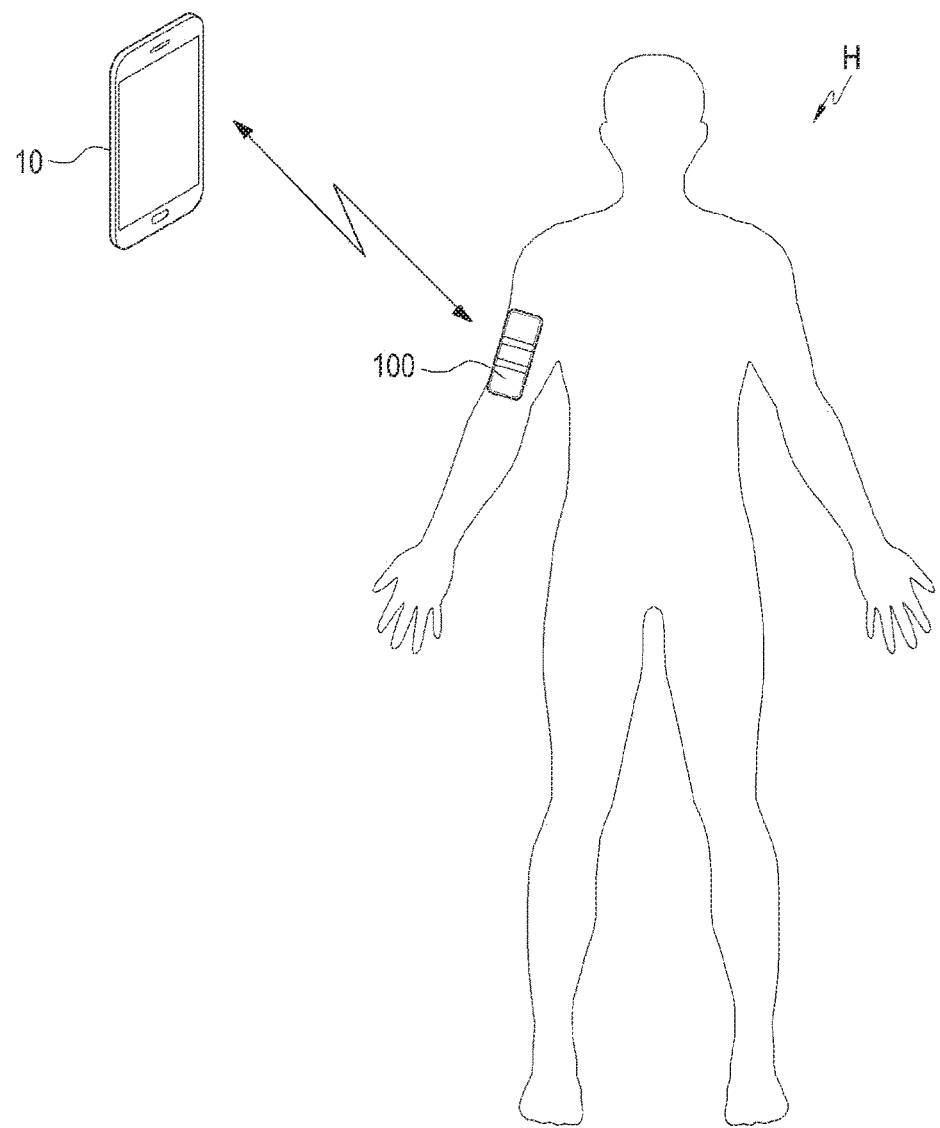
FIG. 11 is a diagram of a bio information measuring device attached to a user's body and communicating with an external electronic device according to an embodiment of the present disclosure.

FIG. 10 is a diagram illustrating an example in which a bio information measuring device 100 remains inserted in the corium H2 of the user H, which is illustrated in FIG. 11) according to an embodiment of the present disclosure. FIG. 11 is a diagram illustrating an example in which a bio information measuring device 100 is attached to the body of the user H and interworks with an external electronic device according to an embodiment of the present disclosure.

Referring to FIGS. 10 and 11, the needle portion 140 may be disposed on the surface of the epidermis H1 that is present on the outermost layer of the skin of the user H. When the bio information measuring device 100 is pressed with a predetermined force with the needle portion 140 disposed on the surface of the skin, the needles of the needle portion 140 may be inserted into the epidermis H1 and the corium H2. Here, since no nerves are dispersed in the epidermis H1 or the corium H2, when the micro needles are put in only up to the corium H2, the testee would not feel pain by the intrusion of the needles. Meanwhile, since the epidermis H1 present on the outermost layer of the skin has the highest impedance, even when the needles are intruded only into the epidermis H1, exact measurement may be achieved. However, more correct measurements may be obtained by intruding the needles up into the epidermis H1 and the corium H2. Here, when the needles are intruded up into the hypodermic tissue H3 under the corium H2 to get more exact measurements regarding bio information, the needles would present only very tiny initial stimulus or pain because the needles are very thin.

As described above, the bio signals measured from the hypodermic tissue H3 of the body by applying the bio information measuring device 100 to the skin may be transferred via the needles and electrodes to an external electronic device 10, e.g., a portable terminal. The separate electronic device (i.e., the external electronic device 10) may store the bio information received from the bio information measuring device 100. When the separate electronic device has a display module, it may display bio information, e.g., the concentration of the blood sugar of the user H and may represent the received bio information in graph or statistics so that the user H may identify variations in the bio information in various ways, e.g., per time or per date.

A method for manufacturing the bio information measuring device 100 is now described. In describing the method for manufacturing the bio information measuring device 100, the above description applies to the above-mentioned components, functions, or operations.

Figure 12:
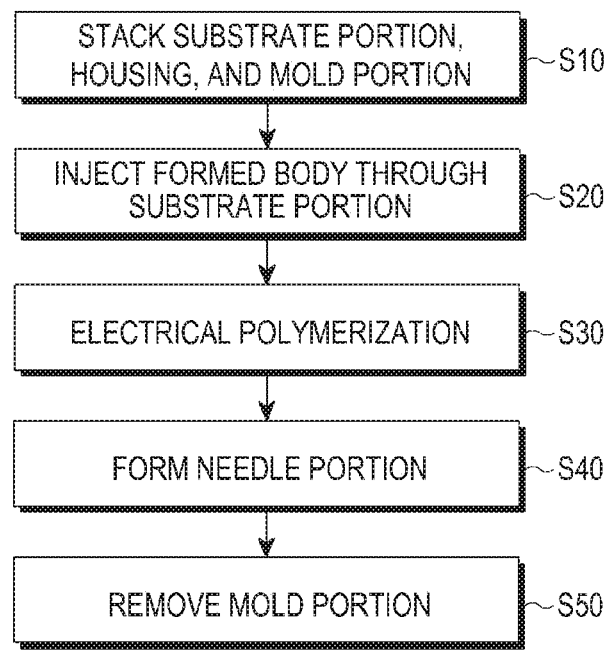
FIG. 12 is a flowchart of a method for manufacturing a bio information measuring device according to an embodiment of the present disclosure.

FIG. 12 is a flowchart of a method for manufacturing a bio information measuring device 100 according to an embodiment of the present disclosure.

Referring to FIG. 12 in conjunction with FIG. 7, according to an embodiment of the present disclosure, the bio information measuring device 100 may be implemented by injecting the biocompatible organic material 141 including the enzyme member 142 and the conductive polymer 143 or the biocompatible organic material 141 including the conductive polymer 143 into the stacked sensor portion 110 and polymerizing and forming it into the needle portion 140.

For example, the housing 130 having the second space portion 135 connecting with the first space portion 125 may be stacked on the substrate portion 120 having the first space portion 125 (at step S10). Specifically, the first body 131 and the second body 132 may be sequentially stacked (i.e., the first body 131 is stacked on top of the second body 132) with the first electrode 122 disposed on the main substrate 121. Further, the mold portion 150 having the concave needle tip 151 shape may be stacked on the second body 132. The second electrode 123 may be provided under the main substrate 121 when providing the first electrode 122 on the main substrate 121, or alternatively, after the mold portion 150 is stacked on the second body 132, the stacked structure may be turned over to be stacked so that the second electrode 123 is stacked corresponding to the position of the receiving portion 126 on the rear surface of the main substrate 121.

As such, by flipping over the structure (hereinafter, a "first stacked set") having the second electrode 123, the main substrate 121, the first electrode 122, the first body 131, the second body 132, and the mold portion 150 stacked from the bottom in the order thereof, the second opening 128 may be exposed through a surface of the first stacked set. When the electrode portion 122 and 123 is provided with two electrodes, each of the second openings 128 of the outlets 123Wb and 123Cb and the inlets 123Wa and 123Ca are exposed to the position of the working electrode (W.E) and the counter electrode (C.E) of the second electrode 123, and thus, the four openings may be exposed. Conversely, when the electrode portion 122 and 123 is provided with three electrodes, each of the second openings 128 of the outlets 123Wb, 123Cb, and 123Rb and the inlets 123Wa, 123Ca, and 123Rb are exposed to the working electrode (W.E), the counter electrode (C.E), and the reference electrode (R.E) of the second electrode 123, and thus, the six second openings 128 may be exposed.

As such, the biocompatible organic material 141 including the enzyme member 142 and the conductive polymer 143 or the biocompatible organic material 141 including the conductive polymer 143 may be injected to the positions corresponding to the inlets of the exposed second openings 128 (at step S20).

For example, the biocompatible organic material 141 including the enzyme member 142 and the conductive polymer 143 may be injected into the second opening 128 of the working electrode (W.E), and at least one of the biocompatible organic material 141 including the conductive polymer 143 and the enzyme member 142 or the biocompatible organic material 141 including the conductive polymer 143 but not including the enzyme member 142 may be injected into the second opening 128 of the other electrode than the working electrode (WE), e.g., the counter electrode (C.E) or reference electrode (R.E).

Further, the biocompatible organic material 141 including the conductive polymer 143 may be injected onto the working electrode area (W.E.A), the counter electrode area (C.E.A), and the reference electrode area (R.E.A). In this instance, the method may include, after the polymerization step, the step of coating the enzyme member 142 or the biocompatible organic material 141 including the enzyme member 142 and the conductive polymer 143 onto the outer surface of the needles formed at the position of the working electrode area (W.E.A).

The biocompatible organic material 141 including the enzyme member 142 and the conductive polymer 143 or the biocompatible organic material 141 including the conductive polymer 143 injected through the second openings 128 fills the receiving portion 126 and flows into the second space portion 135 through the first opening 127 to fill the inside of the second space portion 135 forming a partitioned space in the shape of the electrode portion 122 and 123. Further, the biocompatible organic material 141 including the enzyme member 142 and the conductive polymer 143 or the biocompatible organic material 141 including the conductive polymer 143 may pass through the plurality of openings 132a of the second body 132 to fill the needle tips 151 of the mold portion 150.

As such, the biocompatible organic material 141 including the enzyme member 142 and the conductive polymer 143 or the biocompatible organic material 141 including the conductive polymer 143, which is injected and fills up to the needle tips 151 of the mold portion 150, may be formed by at least one of electrical polymerization, thermal polymerization, photo polymerization, acid polymerization, or base polymerization (at step S30). Here, upon polymerizing the biocompatible organic material 141 including the conductive polymer 143 including the enzyme member 142, the electrical polymerization, among others, may be used to prevent the enzyme member 142 from being destroyed in the polymerization process.

By polymerizing the biocompatible organic material 141 including the enzyme member 142 and the conductive polymer 143 or the biocompatible organic material 141 including the conductive polymer 143, the needles projecting from inside of the sensor portion 110, e.g., the first space portion 125 and the 135, to a side of the sensor portion 110 may be formed as a single body (at step S40). The mold portion 150 may be removed after polymerizing the biocompatible organic material 141 including the enzyme member 142 and the conductive polymer 143 or the biocompatible organic material 141 including the conductive polymer 143 (at step S50).

Further, as mentioned above, when the needles are formed only of the biocompatible organic material 141 including the conductive polymer 143 at the position of the working electrode (W.E) and the electrodes other than the working electrode (W.E), after removing the mold portion 150, the biocompatible organic material 141 including the conductive polymer 143 including the enzyme member 142 may be coated on the surface of the needles projecting at the position of the working electrode (W.E) to react with the reactive substances in the body.

As such, the needle portion 140 may be formed by injecting and polymerizing the biocompatible organic material 141 including the enzyme member 142 and the conductive polymer 143 or the biocompatible organic material 141 including the conductive polymer 143 with the sensor portion 110 stacked, leading to an easier and simpler manufacturing process. Further, as the needle portion 140 is formed with a single body of needles projecting from a space inside the sensor portion 110 to a side of the sensor portion 110, the inside or outside of the needles may be formed of the same composition, and thus, even when the outside of the needles is escaped or rendered to have defects, the same bio information may always be implemented. Further, as the single-bodied needles are formed of a biocompatible material 141a, in case the needles are escaped while remaining intruded in the corium H2 and left in the corium H2, the needles may melt away or dissolve in the corium H2, lowering the danger of use.

While the present disclosure has been shown and described with reference to certain embodiments thereof, it will be understood by those skilled in the art that various changes in form and details may be made therein without departing from the scope of the present disclosure. Therefore, the scope of the present disclosure should not be defined as being limited to the embodiments, but should be defined by the appended claims and equivalents thereof.

What is claimed is:

1. A bio information measuring device, comprising:
a sensor portion including a substrate portion having a first space portion and a housing stacked on top of the substrate portion; and
a needle portion including a needle portion base and a plurality of needles projecting from a plurality of openings formed in a surface of the sensor portion, the plurality of needles configured to pierce tissue,
wherein the plurality of needles include a biocompatible organic material which includes an enzyme member that reacts with an analysis material and a conductive polymer for transferring an electrical signal generated as a result of a reaction of the enzyme member with the analysis material,
wherein the housing includes a second space portion connected to the first space portion, and
wherein the needle portion base is configured to fill the first space portion and the second space portion.

2. The bio information measuring device of claim 1, wherein the plurality of needles are formed using at least one of electrical polymerization, thermal polymerization, photo polymerization, acid polymerization, and base polymerization.

3. The bio information measuring device of claim 1, wherein the biocompatible organic material further includes a filler.

4. The bio information measuring device of claim 1, wherein the substrate portion further includes a main substrate and an electrode portion provided on at least one of a first surface of the main substrate and a second surface of the main substrate, and wherein the first surface of the main substrate and the second surface of the main substrate are disposed in opposing relation to one another.

5. The bio information measuring device of claim 4, wherein the electrode portion includes a first electrode that is provided on at least one of the first surface of the main substrate and the second surface of the main substrate, wherein the first electrode is electrically connected to the needle portion and a second electrode that is provided on the other one of the first surface of the main substrate and the second surface of the main substrate, and wherein the second electrode is connected to an external connector terminal of the bio information measuring device.

6. The bio information measuring device of claim 5, wherein the first space portion of the substrate portion includes a receiving portion formed on the main substrate, a first opening formed on the first electrode and connecting the second space portion with the receiving portion, and a second opening formed on the second electrode, connected to the receiving portion, and configured for injecting one of a first member and a second member.

7. The bio information measuring device of claim 6, wherein each of the first opening and the second opening includes an inlet for injecting the biocompatible organic material including the enzyme member and the conductive polymer into the receiving portion and an outlet for discharging air from the receiving portion as the biocompatible organic material including the enzyme member and the conductive polymer is injected.

8. The bio information measuring device of claim 6, wherein the receiving portion includes a reservoir.

9. The bio information measuring device of claim 5, wherein the electrode portion includes a working electrode as the first electrode and a counter electrode as the second electrode that is positioned around the working electrode.

10. The bio information measuring device of claim 9, wherein a first needle portion included in the needle portion projects on a working electrode area that is connected to the working electrode, and a second needle portion included in the needle portion, which is connected to the counter electrode, projects on a counter electrode area corresponding to a position of the counter electrode.

11. The bio information measuring device of claim 10, wherein the first needle portion and the second needle portion in the needle portion are a single body formed of the biocompatible organic material including the enzyme member and the conductive polymer.

12. The bio information measuring device of claim 9, wherein the electrode portion includes three electrodes, a first needle portion included in the needle portion projects on a working electrode area connected to the working electrode, a second needle portion included in the needle portion projects on a counter electrode area corresponding to a position of the counter electrode around the working electrode area, and a third needle portion included in the needle portion connected to the a reference electrode projects on a reference electrode area corresponding to a position of the reference electrode and neighbors the working electrode area.

13. The bio information measuring device of claim 12, wherein the first needle portion, the second needle portion, and the third needle portion in the needle portion are a single body formed of the biocompatible organic material including the enzyme member and the conductive polymer.

14. The bio information measuring device of claim 9, wherein the second space portion forms a partitioned space of a region corresponding to a position of the working electrode and a region corresponding to either a position of a reference electrode or a position of the counter electrode.

15. The bio information measuring device of claim 14, wherein the second space portion is divided into a first partitioned space and a second partitioned space, wherein the first partitioned space is provided on the first electrode and the needle portion base fills an area on the working electrode with the biocompatible organic material including the enzyme member and the conductive polymer, and wherein the second partitioned space neighbors the first partitioned space and the needle portion base fills an area on the counter electrode with at least one of the biocompatible organic material including the enzyme member and the conductive polymer, or the biocompatible organic material including the conductive polymer.

16. The bio information measuring device of claim 14, wherein the electrode portion includes three electrodes, the second space portion is divided into a first partitioned space, a second partitioned space, and a third partitioned space, wherein the first partitioned space is provided on the first electrode and the needle portion base fills an area on the working electrode with the biocompatible organic material including the enzyme member and the conductive polymer, wherein the second partitioned space is positioned around the first partitioned space and the needle portion base fills an area on the counter electrode with at least one of the biocompatible organic material including the enzyme member and the conductive polymer, or the biocompatible organic material including the conductive polymer, and wherein the third partitioned space neighbors the first partitioned space and the second partitioned space and the needle portion base fills an area on the reference electrode with at least one of the biocompatible organic material including the enzyme member and the conductive polymer, or the biocompatible organic material including the conductive polymer.

17. The bio information measuring device of claim 1, wherein the housing includes a first body and a second body, wherein the first body is formed on the substrate portion and forms the second space portion, and wherein the second body is formed on the first body, the second body including the plurality of openings for connecting to the second space portion and fastening the plurality of needles to the first body.

* * * * *